US010533950B2

(12) United States Patent
Herzog et al.

(10) Patent No.: US 10,533,950 B2
(45) Date of Patent: Jan. 14, 2020

(54) METHOD, DEVICE, AND SYSTEM FOR THE AUTOMATED DETERMINATION OF OPTICAL DENSITIES OR OF THE CHANGE IN OPTICAL DENSITIES OF REACTION MIXTURES IN SHAKEN REACTORS

(71) Applicant: Aquila Biolabs GmbH, Baesweiler (DE)

(72) Inventors: Konrad Herzog, Herzogenrath (DE); David Frank, Herzogenrath (DE)

(73) Assignee: Aquila Biolabs GmbH, Baesweiler (DE)

( * ) Notice: Subject to any disclaimer, the term of this patent is extended or adjusted under 35 U.S.C. 154(b) by 480 days.

(21) Appl. No.: 15/115,349

(22) PCT Filed: Jan. 30, 2015

(86) PCT No.: PCT/EP2015/051911
§ 371 (c)(1),
(2) Date: Sep. 14, 2017

(87) PCT Pub. No.: WO2015/114083
PCT Pub. Date: Aug. 6, 2015

(65) Prior Publication Data
US 2018/0011027 A1    Jan. 11, 2018

(30) Foreign Application Priority Data

Feb. 1, 2014  (DE) .................. 10 2014 100 128

(51) Int. Cl.
*G01N 21/51* (2006.01)
*G01N 21/82* (2006.01)
(Continued)

(52) U.S. Cl.
CPC ............. *G01N 21/82* (2013.01); *C12M 27/16* (2013.01); *G01N 15/06* (2013.01); *G01N 21/51* (2013.01);
(Continued)

(58) Field of Classification Search
None
See application file for complete search history.

(56) References Cited

U.S. PATENT DOCUMENTS 8,405,033 B2 *    3/2013   Debreczeny ........... G01N 15/06
                                                            250/338.1
2005/0219526 A1 *  10/2005  Peng ..................... G01N 21/274
                                                            356/338

FOREIGN PATENT DOCUMENTS

DE     000010125600 A1    12/2002
DE     102004017039 A1    3/2005

OTHER PUBLICATIONS

Samorski et al. "Quasi-continuous Combined Scattered Light and Flourescence Measurements: A Novel Measurement Technique for Shaken Microtiter Plates." Biotechnology and Bioengineering, Oct. 5, 2005, 92(1)61-68.

(Continued)

*Primary Examiner* — Jennifer Wecker
(74) *Attorney, Agent, or Firm* — Wagenknecht IP Law Group, PC

(57) ABSTRACT

A method, a device, and a system for the automated determination of optical densities or of the change in optical densities of reaction mixtures in shaken reactors during shaking operation. The method uses a reaction mixture distribution, which periodically fluctuates because of the shaking action, to record measurement points (20/21) of transmission/scattered-light measurements. All measurement points (20/21) of a measurement operation are combined into a measurement series (34), from which the optical (Continued)

density and/or the change in the optical density, and other process parameters, can be determined with high reliability by means of suitable mathematical methods.

39 Claims, 12 Drawing Sheets

(51) Int. Cl.
| | | |
|---|---|---|
| *G01N 15/06* | (2006.01) | |
| *C12M 3/06* | (2006.01) | |
| *C12M 1/00* | (2006.01) | |
| *G01N 21/17* | (2006.01) | |
| *G01N 15/00* | (2006.01) | |
| *C12M 1/34* | (2006.01) | |
| *G01N 21/59* | (2006.01) | |

(52) U.S. Cl.
CPC ......... *C12M 41/36* (2013.01); *G01N 21/1717* (2013.01); *G01N 21/5907* (2013.01); *G01N 2015/0046* (2013.01); *G01N 2015/0053* (2013.01); *G01N 2015/0693* (2013.01)

(56) References Cited

OTHER PUBLICATIONS

Rivera, Gwendolyn Leialoha, "Development and Characterization of a Parallel Microbioreactor System." Dec. 1, 2004, Retrieved from the internet on Oct. 14, 2016, http://scholarspace.manoa.hawaii.edu/handle/10125/10394.
PCT/EP2015/051911 International Search Report dated Jun. 23, 2015.

\* cited by examiner

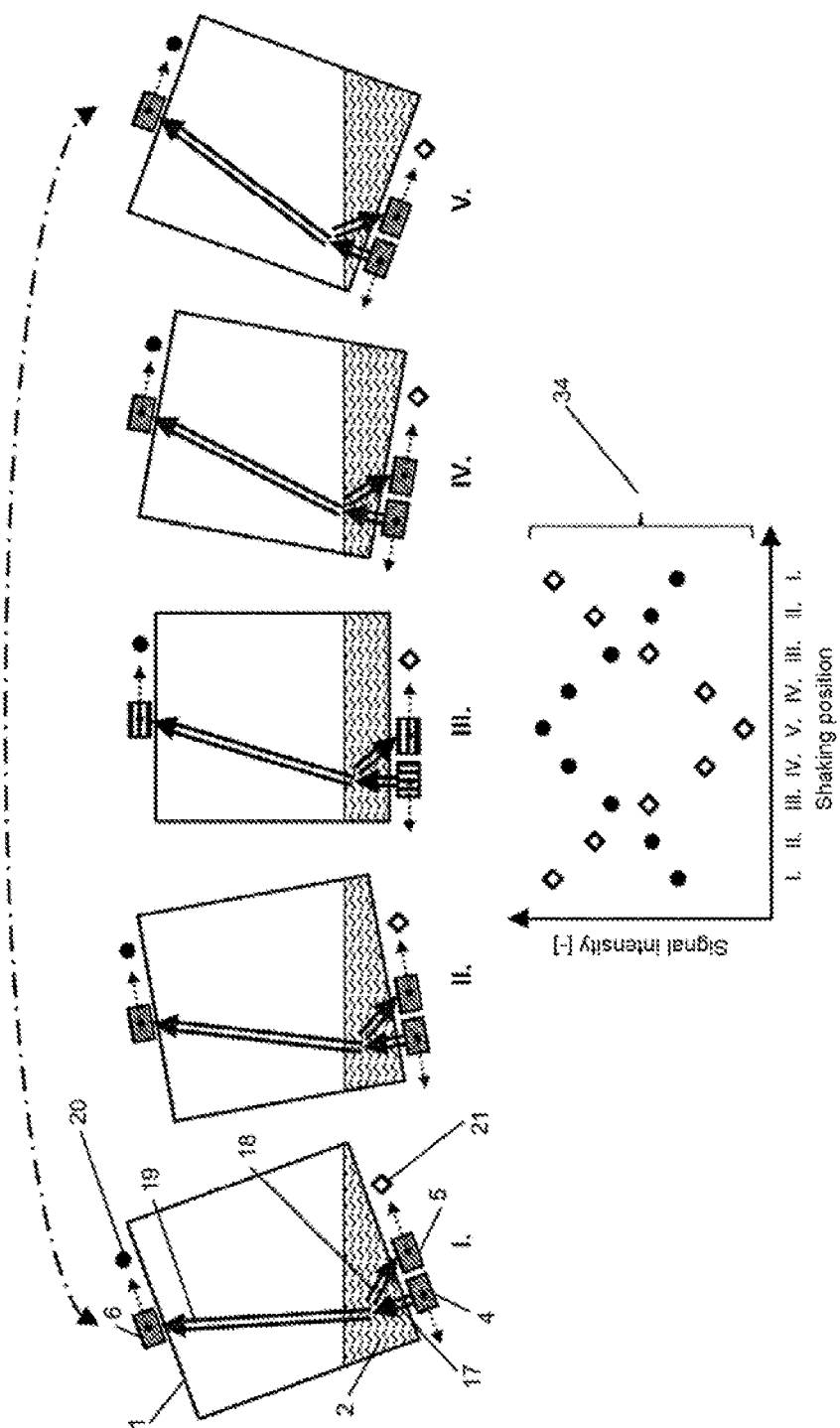

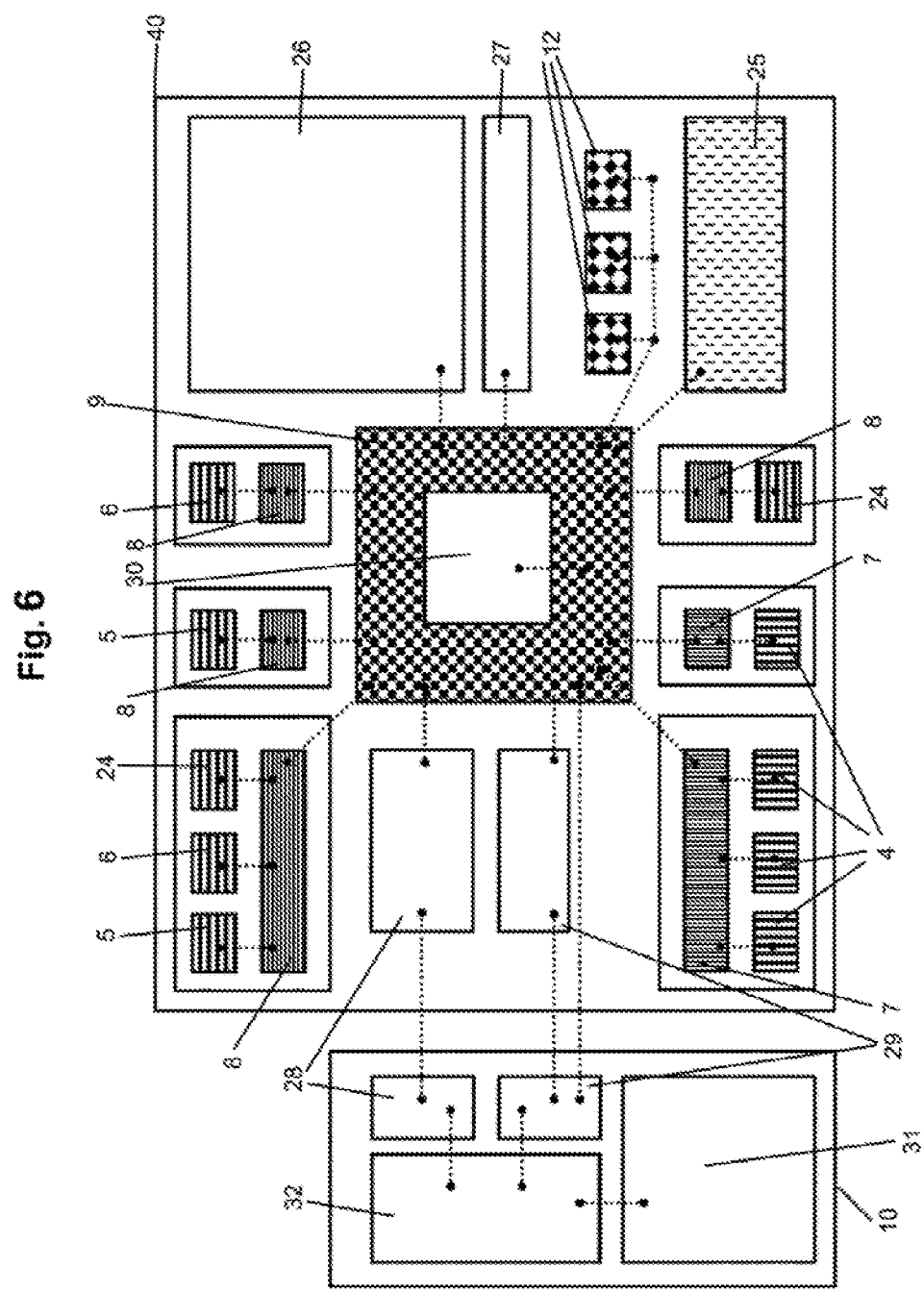

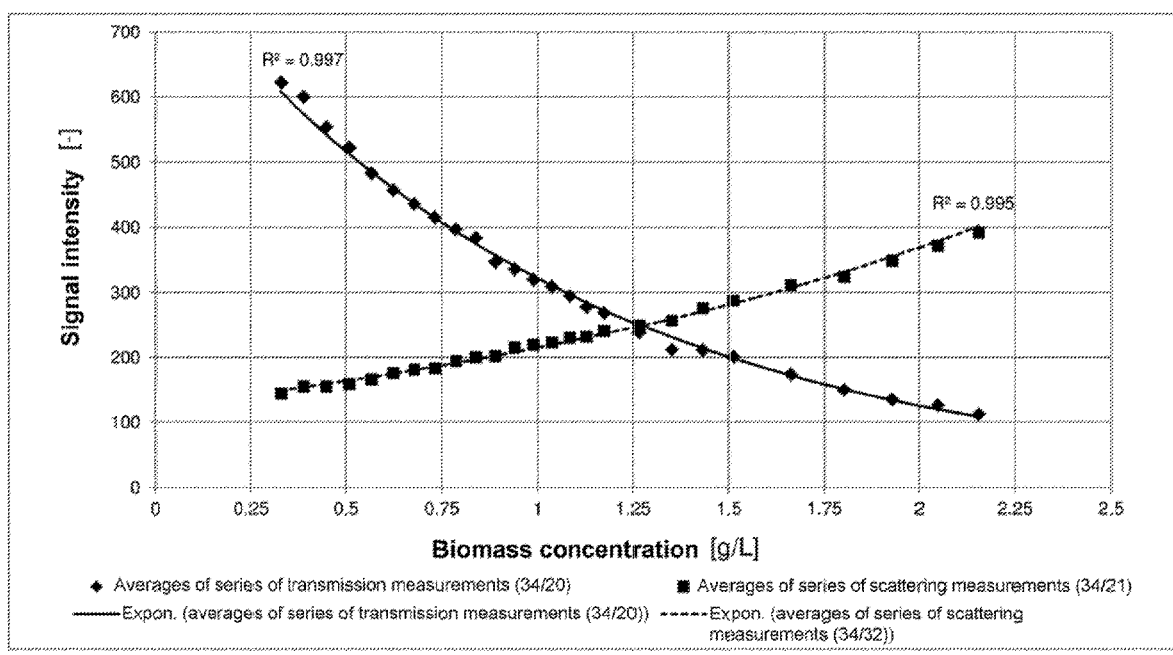

Fig. 11
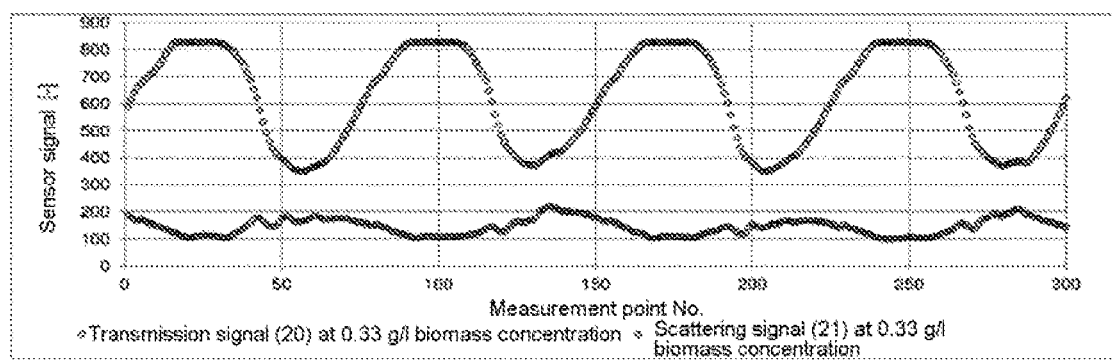
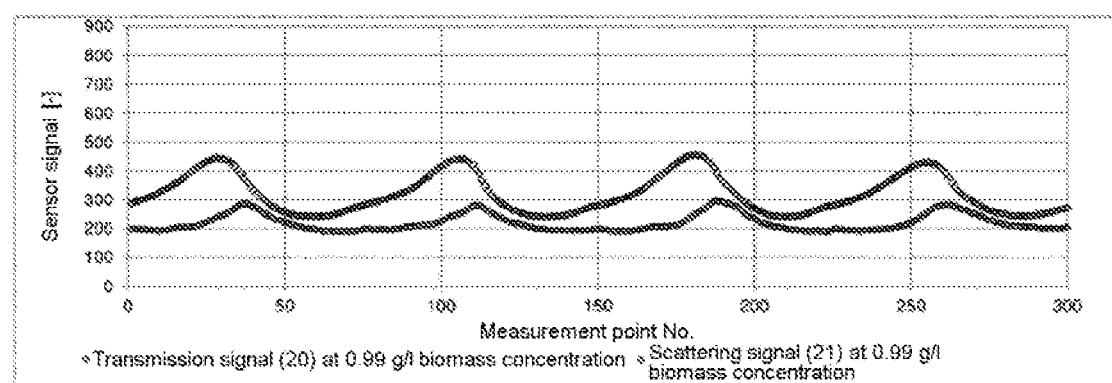
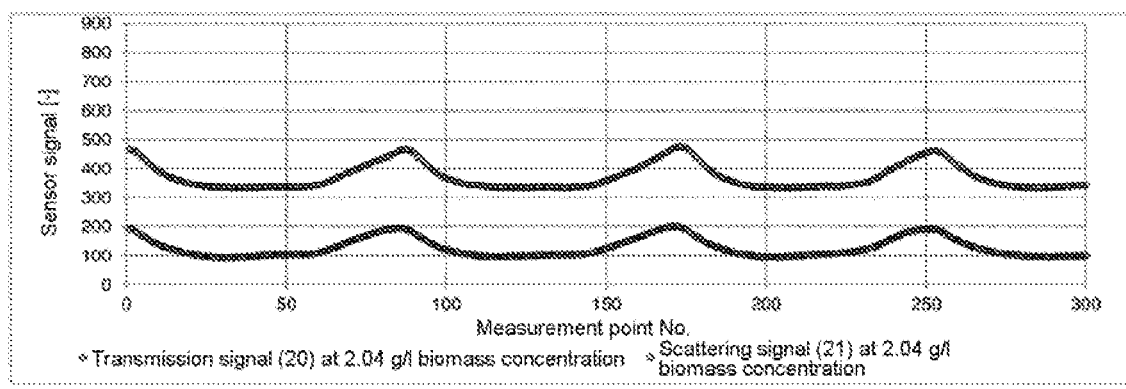

METHOD, DEVICE, AND SYSTEM FOR THE AUTOMATED DETERMINATION OF OPTICAL DENSITIES OR OF THE CHANGE IN OPTICAL DENSITIES OF REACTION MIXTURES IN SHAKEN REACTORS

CROSS REFERENCE TO RELATED APPLICATIONS

This is a US national phase application of international patent application no. PCT/EP2015/051911, filed Jan. 30, 2015, which claims benefit of priority to German patent application DE 102014001284.0, filed Feb. 1, 2014. Each of which is herein incorporated by reference in its entirety herein.

TECHNICAL FIELD

The invention relates to a method, to a device and to a system for the automated determination of the optical density and/or of the change in optical density of reaction mixtures in shaken reactors during shaking operation, it being possible to draw conclusions as to the concentration of at least one component of the reaction mixture from the determined optical densities and/or the changes in the optical density.

BACKGROUND OF THE INVENTION

Various devices and methods for determining the optical density of reaction mixtures in shaken bioreactors are known in the art. The generally known principle behind these technologies is the diffusion and/or transmission of light through matter located on the light path. The diffusion and transmission intensities are in a relationship, which can be modelled mathematically, with the concentration of the matter located on the light path which interacts with the light, and so measuring the intensities of scattered and transmitted light makes conclusions as to substance concentrations possible. Devices for implementing this basic method conventionally consist of at least one light source for introducing light into the volume to be analysed and at least one light sensor for detecting the scattered and/or transmitted light. This underlying construction and the underlying method can be modified to achieve better results. The prior art publications cited hereinafter are therefore only described in so far as they go beyond and improve the generally known methods and devices for determining the optical density of reaction mixtures.

US 2009/0075248 A1 discloses a method and a device for optically determining the particle concentration in a medium over a wide linear range. In this document, a plurality of light source/light sensor pairs are used for measuring scattering and/or transmission signals, which can in turn be combined using various algorithms in such a way that there is a linear dependency between the algorithmically modified measurement signal and the particle concentration in the medium over a range of up to three orders of magnitude of concentration (for example 0.1 g/l to 100 g/l). According to the patent specification, this simplifies the optical determination of the particle concentration in a medium, since the normally non-linear relationship between the particle concentration and a single directly measured signal is transformed into a linear relationship. Various embodiments of the method and device are disclosed, for example for non-invasive measurement of the biomass concentration in a fermenter through the translucent wall thereof, for non-invasive measurement of the biomass concentration in unshaken flasks through the light-permeable walls thereof, or for invasive measurement by means of a measurement probe which can be immersed in the medium.

The primary drawback of the method and device of US 2009/0075248 A1 is that it cannot be used for measurement in shaken systems during shaking operation. The constantly changing shape and distribution of the medium in the shaken vessel during shaking lead to periodically fluctuating strengths of the transmission and scattering signal, which are not taken into account by the disclosed method and device and thus render the method unusable. A further drawback of the disclosed embodiments is that they cannot be applied to a shaken reactor, or can only be applied with poor mechanical stability.

In addition, as regards the method and device of US 2009/0075248 A1, it is doubtful whether the modes of operation, measurement ranges and measurement precisions set out in the patent specification are actually achievable in a real-life application, in particular in shaken systems. The examples set out in the patent specification are only of a limited predictive power, at least for applications in the field of cultivating organisms, since they are carried out on yeast suspensions in aqueous 0.9% NaCl solution. However, the culture solutions used in reality have to contain organic nutrition sources (for example protein lysates, cell extracts, sugars, amino acids, lipids etc.), which also contribute to the strength of the scattering and transmission signal to be measured. This leads to different behaviour of the disclosed linearization algorithms when the same cell concentration is measured in different media, since these algorithms are dependent on signal thresholds, and whether these thresholds are reached is affected to different degrees by different media. The resulting measurement imprecisions are a major drawback of the method and device.

U.S. Pat. No. 8,405,033 B2 discloses a method and a device for the optical determination of the particle concentration in a medium through the side wall of a container. The particle concentration is determined exclusively by way of the scattered light; no transmission signal is measured. So as to be able to work with low liquid levels, a wavelength is used which is strongly absorbed by the medium, in such a way that the measured scattering signal originates merely from a small volume directly in front of the sensor and light source, which are positioned at a distance from one another of at least 10% and at most 1000% of the average penetration depth of the light into the absorbing medium. Various configurations of the method and device are disclosed, for example for non-invasive measurement of the biomass concentration through the side wall or the base of a shaking flask. Further, one sentence mentions recording several measurement points per second so as to observe fluctuations in the liquid level in front of the detector. However, it is not disclosed what measurement purpose this is intended to serve.

A drawback of the method and device of U.S. Pat. No. 8,405,033 B2 is the limitation to measurements on the scattering signal, even though at low particle concentrations (for example cell densities having OD600<0.5) the precision and reliability of transmission measurements are much better than for scattering measurements.

A further drawback of the method and device of U.S. Pat. No. 8,405,033 B2 is the practicability thereof in real appliances. Thus, for correct operation of the "OD scanner" appliance marketed by BugLab LLC, 3350 Clayton Road, Suite 220, Concord, Calif. 94519 on the basis of this patent, a liquid level of at least 3 cm is required in front of the light source and the detector. Specifically when small reaction vessels (for example shaking flasks) are used, this can only be achieved by way of oblique positioning, meaning that the measurement cannot be taken during shaking operation. Measurements by way of a system attached below the flask as proposed in the patent also cannot be implemented in practice for the small volumes of media and reaction vessels frequently used in the industry (for example 20 ml in a 200 ml shaking flask), since the required fill levels cannot be reached for conventional flask fill amounts of 10%. Therefore, so as to be able to take continuous measurements during shaking operation on the basis of this patent, measurements either in very large medium volumes (for example 200 ml in a 2000 ml shaking flask) or in considerably overfilled shaking flasks (fill amount>>10%) would be required. Neither of these variants makes any sense, since overfilled shaking flasks have very poor mixing and oxygen transfer rates which cannot be scaled to other reactor systems, and large-volume shaking flask experiments go against the principle of minimised high-throughput screening.

In addition, as regards the method and device of U.S. Pat. No. 8,405,033 B2, as was the case for US 2009/0075248 A1, it is doubtful whether the modes of operation, measurement ranges and measurement precisions set out in the patent specification are actually achievable in a real-life application, in particular in shaken systems. The examples set out in the patent specification were also carried out on yeast suspensions in aqueous 0.9% NaCl solution, and are only of limited predictive power, as per the arguments regarding US 2009/0075248 A1, at least for applications in the field of cultivating organisms. In particular in the aforementioned measurement range of low particle concentrations, the scattered light measurement can be distorted by typically optically active substances in the medium. The calibration of the measurement appliance to each newly used medium, as required to correct the error, is therefore an additional drawback.

JP 02/012217426 A discloses a method for contactless, continuous measurement of the growth of a sample during cultivation. The basic functional principle of the method is transmitted and scattered light measurement at a position where there is only a very low liquid thickness as a result of the liquid distribution occurring during shaking, in such a way that evaluable transmission measurements can be carried out. Further, the possibility of measurement value correction using various parameters is disclosed. Automated addition and removal of culture media with feedback to the measurement values is also mentioned. Adaptation of the light source and detector position with feedback to the measurement values for the best possible optimisation of the measurement is also disclosed.

A drawback of the method of JP 02/012217426 A is the low width of the measurement range (maximum OD600=20) derived from the patent, meaning that measurements cannot be taken at higher cell densities. In the low concentration range (OD600<1), the precision of the method is poor, as can be seen from the examples set out in the patent specification. These drawbacks are also apparent from the product manufactured by the patent proprietor, TAITEC Corp., 2693-1, Nishikata, Koshigaya City, Saitama, Japan, the measurement range of which, at OD600 values between 0.1 and 2.0, is much narrower and thus of less use than for the aforementioned prior art patents.

A further major drawback of JP 02/012217426 A is the strong dependency of the measurement on the shaking frequency (JP 02/012217426 A, Table 2). To apply the method at different shaking frequencies, specific correction or calibration data are therefore required in each case, and recording these constitutes a drawback in application in practice.

A further drawback of the method of JP 02/012217426 A is the susceptibility thereof to ambient light. The measurement on particularly thin liquid layers using a light source and a detector can lead to distortion of the measurement due to ambient light sources. The patent does mention that the use of infrared light can eliminate this source of error; however, conventional light bulbs and the heated walls of temperature-controlled incubators both generate non-negligible amounts of infrared radiation, and can thus also contribute to measurement errors.

An additional drawback of the method of JP 02/012217426 A is the manner in which the light sensors and light sources are arranged, as disclosed in the embodiment and implemented in the corresponding product ("OD-Monitor") from TAITEC Corp., 2693-1, Nishikata, Koshigaya City, Saitama, Japan. In particular but not exclusively in relation to measurement on thin liquid levels as disclosed in the patent, measurement in parallel with the shaking plane has the major drawback that specific shaking frequencies, reactor shapes and fill levels are required so as to bring the medium to be analysed into the optical path between the light source and the light sensor. This disadvantageously limited the universal use of the device for different reactor sizes, shapes and fill levels. In addition, changes, due to the process, in the physical and fluid-dynamic parameters of the shaken medium lead to the thickness of the liquid level located on the light path changing, and this can lead to significant measurement errors or even to complete immeasurability (in the complete absence of a liquid film in the optical path). Examples of changes of this type in the medium are the change in viscosity due to the increase in biomass, due to filamentous growth or due to the secretion of gel-forming substances and the change in the medium volume due to evaporation effects.

U.S. Pat. Nos. 6,673,532 B2 and 7,041,493 B2 disclose a method and a device for the optochemical observation of bioprocesses. Among other things, very generally the possibility of determining the optical density of the culture broth by way of transmission measurements is also disclosed. Likewise, the possibility of a process carried out while shaking and the addition of fluids into the culture broth with feedback to measured parameters are mentioned.

A drawback of the method and device of U.S. Pat. Nos. 6,673,532 B2 and 7,041,493 B2 is the invasive nature of the optical-fibre-based measurement of the optical density, since it results in a high risk of contaminating the culture broth. In addition, this method of measuring optical densities can only be implemented with great difficulty and with mechanical instability in reactors having a shape other than an ideal cylinder shape (for example shaking flasks). The lack of scattered-light-based measurements of the optical density is also a major drawback, since transmission measurements by the method set out therein have a high susceptibility to errors and measurement imprecision at higher biomass concentrations (for example OD600>3) as a result of the very low transmissivity in these cases. At even higher biomass concentrations, such as occur for example in high-cell-density fermentations, the transmissivity falls towards zero, in such a way that evaluable measurement results can no longer be achieved in these cases without scattered light analyses.

A further drawback of the method and device of U.S. Pat. Nos. 6,673,532 B2 and 7,041,493 B2 is the need to use a shaker and positioning table specifically matched to the optical devices, since this means that pre-existing shaking appliances cannot be expanded with an analysis device. The combination set out in the patents of a positioning table having a dispenser for adding fluids to the culture broth is also disadvantageous, since the use of one dispenser for a plurality of reactors brings the risk of cross-contamination. Thus, during the dispensing process, droplets and aerosols from a reactor which are produced by the shaking movement can come into contact with the dispenser, which subsequently passes them on to another reactor during the next dispensing process, thus potentially contaminating it with foreign cells and biomolecules or toxic medium constituents.

DE 10 2004 017039 A1 discloses a method and a device for detecting process parameters of reaction liquids in a plurality of shaken microreactors. The determination of the biomass concentration by way of scattered light measurements is also part of the description.

A drawback of the method and device of DE 10 2004 017039 A1 is the lack of transmission measurements, leading to a worse precision of measurements at low cell densities (for example OD600<0.5) as stated previously. A further drawback is the limitation of the method and device to microreactors, even though many biotechnological, biochemical, microbiological, pharmaceutical and chemical screening processes are carried out at volumes>1 ml.

A further drawback of the method and device of DE 10 2004 017039 A1 is the idea of measurement on a shaken reactor using a stationary, unshaken light source/detector combination. The pulsed illumination of the reactor tuned to the shaking movement, as required for this method and disclosed in the patent, does guarantee that the light is always incident at the same point on the reactor. However, this method can only provide correct measurement data if the same part of the liquid distribution due to shaking is also always located at the measurement position at the moment of each measurement. However, as a result of the aforementioned changes in liquid volume and viscosity which accompany the process, the liquid distribution due to shaking in the reactor may change in such a way that the corresponding relative measurement position within this liquid distribution also changes, in such a way that the measurement results are no longer comparable with the results recorded earlier in the process, and correct determination of the optical density is no longer possible with the occurring fluid-mechanical changes.

All methods and devices known in the art for determining the optical density and/or the change in the optical density of reaction mixtures in shaken reactors are based on an underlying measurement approach which attempts to use particular measures to minimise or eliminate the effect on a measurement from the movement of the reaction mixture in the reactor due to shaking. The measures used for this purpose are for example interrupting the shaking (U.S. Pat. No. 8,405,033 B2), selecting a light path on which the movement of the reaction mixture due to shaking is minimal (JP 02/012217426A), immersing optical fibres to optimise the light path (U.S. Pat. Nos. 6,673,532 B2 and 7,041,493 B2) and using flash lamps tuned to the shaking frequency as a light source (DE 10 2004 017039 A1).

SUMMARY OF THE INVENTION

Starting from this prior art, an object of the invention is to set out a method for the automated determination of the optical density and/or of the change in the optical density of reaction mixtures in shaken reactors during shaking operation which works reliably under a wide range of process conditions. This reliability of the measurement of the optical density and/or of the change in the optical density of reaction mixtures in shaken reactors includes, in particular but not exclusively, reliable measurement in ambient light, reliable measurement at different fill levels of the reactor, reliable measurement at different shaking frequencies, reliable measurement with minimised calibration outlay, reliable measurement in turbulent systems, and reliable measurement at both low and high optical densities. Further, the method to be set out should make possible the automatic determination of further characteristic parameters of the reaction mixture or of the reaction, and make possible a reliable intervention, tuned to the measurement results and parameters, in the reaction sequence. In addition, a device and a system for carrying out the method are to be set out.

In one aspect of the invention a method for determining the optical density and/or the change in the optical density of a reaction mixture in a shaken reactor is provided, which includes providing light from at least one light source that enters the reaction mixture, detecting the light exiting the reaction mixture by at least one light sensor, shaking the reactor and the reaction mixture during the detection of the light by the at least one light sensor, wherein the light detected by the at least one light sensor is at a frequency such that the shaking frequency is not an integer multiple of the detection frequency, and combining at least two measurement points detected by at least one light sensor in a particular time interval into a series of measurements.

In a related aspect of the invention a device is provided, which includes at least one light source, which is positioned and orientated in such a way that the light emitted thereby can enter the reactor and directly and/or indirectly enter the reaction mixture under the conditions of at least one type of shaking, at least one light sensor, at least one light sensor being positioned and orientated in such a way that it can directly and/or indirectly detect light emitted from the reactor and/or the reaction mixture, wherein the at least one light sensor is positioned and orientated in such a way that the light detected thereby and emitted from the reactor and/or the reaction mixture has periodic changes due to shaking in at least one of the properties thereof, but in particular the intensity thereof, and at least one processor and/or is operated in combination with at least one processor, at least one processor being used for at least one of the following purposes: recording the measurement values, storing the measurement values, processing the measurement values, representing the measurement values and/or processing results.

BRIEF DESCRIPTION OF THE DRAWINGS

FIG. 3 shows by way of example, for a reactor 1 under rocker shaking, the dependency of the measured light intensities on the shape and distribution of the reaction mixture 2 in the reactor 1.

FIG. 6 is a schematic drawing of a non-modular embodiment of the device.

FIGS. 10 to 14 show example measurement and evaluation results which were obtained by the method according to the invention.

DETAILED DESCRIPTION OF THE INVENTION

Figure 1:
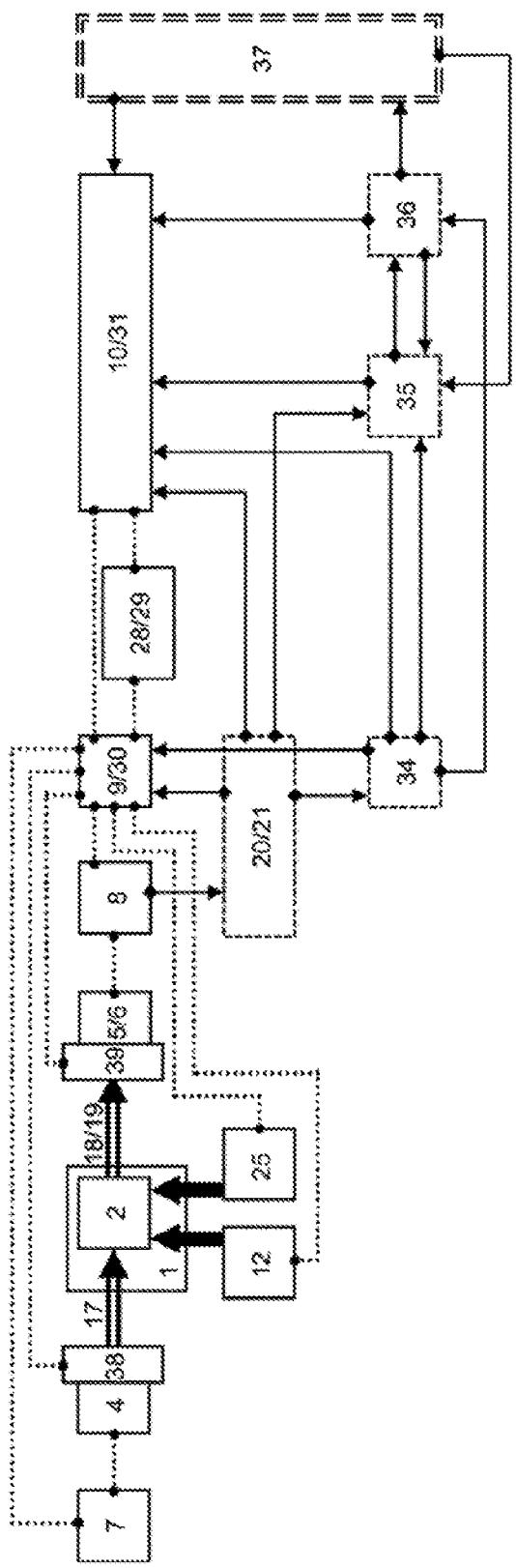
FIG. 1 is a schematic drawing of a general embodiment of the method and of the device.

The invention can be used in particular for the automated determination of the optical density and/or of the change in the optical density and for the automated calculation of further parameters and properties of the reaction mixtures of processes of cultivating cells and organisms, processes of enzymatic, biochemical and chemical reactions, and other processes involving reaction mixtures, in which the reaction mixture is continuously shaken.

The optical density and/or the change in the optical density and/or fluid-mechanical parameters and properties of the reaction mixture can be determined directly from the measurement values determined on the basis of the invention. By way of suitable mathematical methods, models and algorithms, further parameters and properties of the reaction mixture can be determined from these data in parallel with carrying out the process, for example growth rates, substrate affinities, dissociation constants, inhibition constants, catalytic conversion rates, oxygen transfer rates, activation constants, repression constants, and substrate or product concentrations.

The invention is intended for use in particular in shaken reactors, such as shaking flasks and T-flasks having fill volumes of less than one liter, so as to reduce the currently high measurement complexity for biotechnological, pharmaceutical, chemical and biochemical screening, optimization and process monitoring methods and so as to make these methods highly parallel and simultaneously low in staff outlay for measurement analysis and evaluation. Also, as a result of the non-invasive measurement method of the invention, the risk of contamination from the measurement methods based on sampling which are currently predominantly used should be reduced to virtually zero. The invention should make robust measurements on shaken reactors during shaking operation possible in a wide range of use conditions, delimiting it from the prior art. This is of particular importance because interruptions to the shaking operation (for example for the purpose of measuring optical densities) can seriously affect the progression of a reaction taking place in a reaction mixture, in such a way that in many cases results from shaken processes can only be transferred with great difficulty and considerable errors to processes which are stirred or mixed in some other manner. The use of the invention is intended to solve this problem.

Definitions

In relation to the following description of the invention and in relation to the claims, the following definitions are set.

Reactors are containers which are used in particular but not exclusively for cultivating organisms. Further fields of use of reactors are, among others, biocatalytic processes using organisms and/or biomolecules and other chemical and/or physical processes, processes meaning, in particular but not exclusively, all types of conversion, separation, combination, mixing, change in size of, in particular but not exclusively, chemical substances, organisms, particles, solutions, emulsions and foams. Reactors within the meaning of the invention include, in particular but not exclusively, shaking flasks, T-flasks, microtitre plates, deep well plates, shaking vats, fermentation bags, multi-purpose test tubes and cell culture dishes.

A reaction mixture is a homogeneous or heterogeneous mixture of at least two components, which differ in at least one physical, chemical or biological property. Components include, in particular but not exclusively, organisms and biomolecules in accordance with the above description, chemical substances, particles, solutions, emulsions and foams.

Organisms include, in particular but not exclusively, single-cell and multicellular prokaryotic and eukaryotic creatures or the lysates thereof and natural or synthetic systems of basic biomolecules, which include, in particular but not exclusively, nucleic acids, proteins, sugars and lipids.

The optical density E is a wavelength-dependent measure of the change in intensity of electromagnetic radiation when traversing a medium, and is usually described as $$E = \log_{10}\left(\frac{I_0}{I}\right)$$

where $I_0$ is the light intensity before traversing the medium and I is the light intensity after traversing the medium. Accordingly, the change in optical density $\Delta E$ is:

$$\Delta E = E_2 - E_1 = \log_{10}\left(\frac{I_1}{I_2}\right)$$

The optical density is influenced by a number of interactions between the electromagnetic radiation and the medium, in particular but not exclusively by absorption, diffraction, scattering and reflection. If the traversed medium is a mixture, each component of the mixture contributes, with a component-dependent component and in a component-dependent manner, to the interaction between the electromagnetic radiation and the medium and thus to the optical density. As a result of these properties, the optical density is also a measure of the concentration of the components in the traversed medium. According to the Beer-Lambert law, in homogeneous diluted solutions there is a linear relationship between the optical density and the concentration of the transmission-reducing components.

A light sensor means any device suitable for detecting light from the reactor and/or the reaction mixture and/or the environment and/or directly from a light source, in that at least one changing property of the detected light (in particular the intensity) induces an electrical reaction in the sensor (for example changing an electrical voltage, an electrical potential, an electrical current) which can be detected/read and/or processed/converted/stored by further electronic components (for example analogue-digital converters, operational amplifiers, comparators, resistors, capacitors etc.). A measurement point is thus a direct or processed/modified representation of the electrical reaction in the sensor at a particular time. Light sensors within the meaning of the invention include, in particular but not exclusively, photodiodes provided individually or in an array, photoresistors and phototransistors, and 1D CCD chips (line sensors), 2D CCD chips, 1D CMOS APS chips (line sensors), 2D CMOS chips, and light sensors having a fluorescent coating (for example for UV detection).

A light source means any device suitable for shining light into the reactor and/or the reaction mixture. Light sources within the meaning of the invention include, in particular but not exclusively, LEDs, OLEDs, lasers, light bulbs, fluorescent tubes, flash lamps and combinations of these light sources having at least one fluorescent layer.

Shaking within the meaning of the invention is the periodically repeated translation and/or complete or incomplete rotation of the reactor along at least one translation path and/or about at least one rotation axis. Typical types of shaking are, in particular but not exclusively, orbital shaking (translation of the reactor along a translation path which is closed on itself, generally circular, and positioned in the shaking plane) and rocking shaking (incomplete rotation of the reactor about at least one rotation axis which is non-parallel and generally orthogonal to the gravitational force vector).

A processor means any electronic device which can store data (in particular arithmetical and logical data) and process them on the basis of programmable rules. Processors within the meaning of the invention include, in particular but not exclusively, microcontrollers, microprocessors, system-on-a-chip (SoC) processors, PCs and servers.

Suitable mathematical methods and computing algorithms within the meaning of the invention are all methods and algorithms which can expediently and usefully be used for processing and/or evaluating data which are measured and/or calculated and/or derived from measured data and/or otherwise determined or produced in accordance with the invention.

A series of measurements within the meaning of the invention is a collection of measurement points consisting of at least two measurement points, which have been recorded in a sufficiently short measurement period, in which the optical density of the medium can be considered constant for measurement purposes, by comparison with the process speed. It may be time-dependent. A series of measurements may consist both of measurement points from a single light source/light sensor pair and of a combination of measurement points from different light source/light sensor pairs.

A time series within the meaning of the invention is a temporally ordered collection, consisting of at least two elements, of elements generated at different moments, the associated generation time being assigned to each element. Elements of a time series may, in particular but not exclusively, be measurement signals/measurement points, series of measurements and process parameters/properties.

Solution

The object is achieved on the basis of the underlying principle of determining optical densities by measuring the transmission through and/or scattering in matter located on the light path, using at least one light source/light sensor pair, the reliability of the measurements as required by the object being achieved in that measurement points for the transmission and/or scattering intensity of the light emitted by at least one light source and interacting with the reaction mixture are recorded by at least one light sensor at a measurement frequency such that the shaking frequency is not an integer multiple of the measurement frequency, the measurement frequency being higher than the shaking frequency in an advantageous embodiment of the invention in an advantageous embodiment of the invention, the light source(s) and light sensor(s) are positioned and orientated in such a way that at least one light path extends non-parallel to the shaking plane and/or to the shaking axis.

The object is achieved, in a delimitation from the underlying measurement approach of the prior art, on the basis of the finding that the periodically fluctuating distribution and/or shape of the reaction mixture in the reactor due to the shaking process can be exploited so as reliably to determine the optical density and/or the change in the optical density of the reaction mixture. What is crucial is that a plurality of measurement points (for example scattering and/or transmission intensities) are recorded in a period which is short by comparison with the process speed (for example microbial growth rate or enzymatic reaction speed). The result of a series of measurements of this type is at least one curve which fluctuates periodically as a result of shaking and the shape of which is brought about by the periodically fluctuating levels of the reaction mixture in the relevant light path.

The use of a sufficiently short measurement time by comparison with the process speed makes it possible to record an optical density which is constant for measurement purposes in this period, in such a way that in the ideal, completely undisturbed scenario the measurement curve is a function, dependent on the optical density, of the reaction mixture distribution and/or shape in the reactor. Since the distribution and/or shape of the reaction mixture in the reactor due to the periodic shaking are functions of time, the ideal, completely undisturbed measurement curve is also a mathematically modellable function of time.

In the real-life scenario, each individual measurement signal is affected not only by the optical density and the thickness of the reaction mixture located on the light path, but also by other external factors, in particular but not exclusively by ambient light and inhomogeneities in the reaction mixture (for example bubbles, large particles). These disturbing factors lead to outliers in the ideal curve progression of a series of measurements.

By using suitable mathematical methods, in particular but not exclusively methods from statistics, regression analysis, optimisation and adjustment theory, outliers due to external factors in the curve progression of a series of measurements can be detected, in such a way that the optical density and/or the change in the optical density of the reaction mixture can be reliably determined from a series of measurements.

Since, assuming an optical density which is constant for measurement purposes, the curve progression of a series of measurements is a representation of the distribution, shape and movement of the reaction mixture in the reactor, each series of measurements can also be used for qualitative assessment and/or quantitative determination of fluid-mechanical properties and parameters. This is of particular practical relevance both for in-depth understanding of the analysed process and for scalability of the process building on this understanding (for example upscaling microbial cultivations from small shaking flask fermentations to large stirrer tank reactor fermentations).

Although the fill level of the reactor and the shaking frequency affect the distribution and/or shape of the reaction mixture in the reactor, the basic periodicity of the movement of the reaction mixture in the reactor due to shaking is maintained, aside from in a few extreme and unrealistic edge cases (for example a completely filled reactor). As a result, the invention makes reliable determination of the optical density and/or of the change in the optical density, by suitable mathematical methods for evaluating the series of measurements, possible over a very wide range of fill levels and shaking frequencies. The necessary existence of a periodic fluctuation in the distribution and/or shape of the reaction mixture is crucial for the breadth of the field of application of the invention.

The periodic fluctuations in the thickness of the reaction mixture located on the light path can make the reliable determination of the optical density and/or of the change in the optical density possible merely by measuring the transmission. In addition, by way of suitable mathematical methods, the optical density and/or the change in the optical density can be calculated from the periodically fluctuating curve progression of a series of measurements to a high reliability even in ranges outside the conventional resolution of commercially available spectrometers (for example OD600<0.1).

The additional measurement of at least one scattering signal can be used to verify the transmission data, and extends the measurement range of the method and device into regions of high optical densities, in which reliable determination of the optical density and/or of the change in the optical density is no longer possible even from the periodically fluctuating series of transmission measurements.

The measurement of at least one scattering signal and at least one transmission signal can also be exploited so as to detect foam formation on shaken liquid reaction mixtures, since the foam formation primarily affects the transmission signal, and so during the foam formation the measured scattering intensities no longer match the measured transmission intensities.

As a result of the reliability made possible by the invention when measuring optical densities and/or the change in optical densities, many of the calibration measurements and measurement value corrections mentioned in the art for eliminating effects which affect measurement values, such as ambient light, shaking frequency and reactor fill level, can be omitted.

By using at least two light source/light sensor light paths, system-internal calibrations can if necessary be made at the start of each process and also during the process.

From the optical density and/or change in the optical density determined from at least one series of measurements, the concentration of the optically dense components can be calculated directly by suitable mathematical methods, in particular but not exclusively the concentration of cells, particles and dissolved, emulsified or foamed-in substances.

In an advantageous embodiment of the invention, there is no relative movement between the reactor, the light source(s) and the light sensor(s) during the recording of a series of a measurements.

In an advantageous embodiment of the invention, the measurement frequency is at least two orders of magnitude higher than the shaking frequency (for example shaking frequency of 3 Hz, measurement frequency of 300 Hz). As a result, a sufficient number of measurement points for a series of measurements to make robust mathematical evaluation of the series of measurements possible can be collected within a single shaking period. Accordingly, by way of the high measurement speeds, high temporal densities of the optical densities and/or changes in the optical densities can also be implemented from the series of measurements, and make close monitoring of the analysed process possible.

The data density thus achieved in turn makes possible the reliable and statistically robust application of suitable mathematical methods for deriving further process parameters from the time series of the optical density and/or of the change in the optical density. Mathematical methods of this type include, in particular but not exclusively, adjustment calculations ("curve fitting") and optimisations of model functions to the measured time series of the optical density (for example microbial growth models, enzyme kinetics models).

In accordance with the selected model function, different parameters can be determined, in particular but not exclusively growth rates, substrate affinities, dissociation constants, inhibition constants, catalytic conversion rates, oxygen transfer rates, activation constants, repression constants and substrate or product concentrations.

The selection of the model function can be made by the user or automatically by the software as part of the method.

If there are no model functions adaptable to the temporal progression of the optical density, the change in the optical density and/or other parameters and properties of the reaction mixture, existing model functions can be modified automatically using suitable mathematical methods and computing algorithms so as to make mathematical modelling of the parameters and/or properties possible. For this purpose, model functions can also be automatically generated afresh using suitable mathematical methods and computing algorithms. Methods of this type include, in particular but not exclusively, any type of linear and non-linear optimisation methods and heuristic and directed search algorithms, which include, in particular but not exclusively, linear searches, search tree algorithms, graph-theoretical search algorithms, optimising search methods, direct search methods, evolutionary algorithms, neural networks, and random search methods such as "simulated annealing" or Monte Carlo algorithms.

The suitable mathematical methods and computing algorithms which can be used for automatic qualitative assessment and/or quantitative determination of fluid-mechanical properties from the series of measurements include, among others, the aforementioned methods.

In an advantageous embodiment of the invention, all of the required mathematical methods and computing algorithms are implemented in a cohesive software and/or in individual software modules.

In an advantageous embodiment of the invention, the device is of a modular construction, in such a way that a plurality of reactors and reaction mixtures can be analysed and evaluated by way of at least one shared arithmetic-logic unit and at least one jointly used software, at least one light source/light sensor pair being assigned to each reactor.

In an advantageous embodiment of the invention, the spectral range of the light shone into the reactor and reaction mixture can be selected depending on the process requirement, so as to take into account the wavelength-dependent interaction of the shone-in light with at least one component of the reaction mixture. However, this is not advantageous exclusively for optimising the scattering signal in various cell types and cell sizes in the cultivation of organisms, since the light scattering is dependent on the size of the scattering particle. Thus, for example, bacteria scatter optimally at shorter wavelengths than yeasts or human cells. The selection of a spectral range for shining into the reactor and reaction mixture may be made, in particular but not exclusively, by using light sources having restricted spectral ranges (for example LEDs, OLEDs, RGB LEDs) or by way of spectrally wideband light sources (for example light bulbs, flash lamps) in combination with spectrally selective optics (in particular filters, prisms, diffraction gratings).

In an advantageous embodiment of the invention, the spectral range detected by at least one light sensor can also be selected, it being possible, in particular but not exclusively, to use light sensors having particular spectral properties (for example a very narrow detectable wavelength range) or spectrally wideband light sensors in combination with spectrally selective optics (in particular filters, prisms, refraction gratings).

On the basis of the unprocessed series of measurements, the optical densities and/or changes in the optical density determined therefrom, the fluid-mechanical parameters determined from the series of measurements, and the further process parameters determined from the time series of the optical densities and/or of the change in optical densities and/or of the fluid-mechanical parameters, an automatic intervention in the process sequence is possible, by way of an automatic addition of further components to the reaction mixture, tuned to the measurement values and parameters, for example so as to keep particular parameters constant or affect the change therein in a planned manner. Examples of components to be added are, in particular but not exclusively, reactive substances, emulsifiers, enzyme solutions, cell suspensions, substrates of microbial growth, trace elements, protein expression inductors and repressors, antibiotics, growth factors, pH adjusters, antifoaming substances and solvents.

For the automated addition of components to the reaction mixture, metering systems may be used, such as, in particular but not exclusively, pumps or gravity-driven systems. In an advantageous embodiment of the invention, the metering systems should make possible the electronically controllable addition of variable amounts of the component to be added, for which purpose, in particular but not exclusively, any type of valves and controllable pump systems may be used. The metering system is controlled by a control software, which is integrated into the analysis/evaluation software in an advantageous embodiment of the invention.

In an advantageous embodiment of the invention, the opening of the metering system, via which the components are added into the reaction mixture, is located above the maximum level of the reaction mixture in the reactor achievable during the shaking, in such a way that direct contact between the metering system and the reaction mixture can be prevented so as to reduce or completely eliminate the risk of contamination of the component in the reservoir of the metering system.

In an advantageous embodiment of the invention, each reactor is assigned its own metering system, so as to prevent cross-contamination and make possible continuous additions in parallel in a plurality of reactors.

A further possibility for influencing the process with feedback to the parameters and properties determined from the optical measurements is to temperature-control the reactor and/or reaction mixture. In an advantageous embodiment of the invention, electronically controllable temperature control devices are used for this purpose, in particular but not exclusively Peltier elements and liquid-filled cooling and/or heating jackets.

Fields of application of the process control by way of temperature control are, in particular but not exclusively, the cultivation of organisms, the production of biomolecules using organisms, enzymatically or otherwise catalysed processes and non-catalysed processes having thermodynamic changes accompanying the process. The desired temperature control makes it possible to influence parameters such as growth and/or reaction speeds, protein expression rates, product stability (in particular protein stability and protein folding), solubility, activation energy etc.

Figure 9:
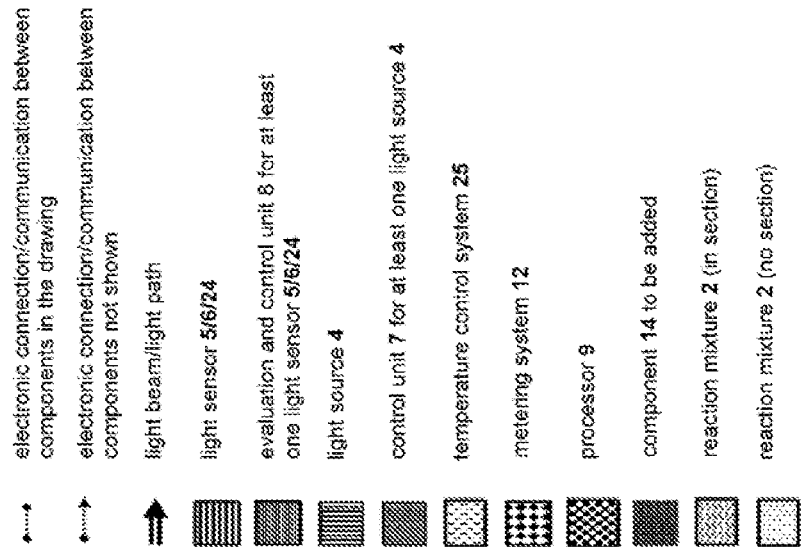
FIG. 9 is a graphical legend explaining some of the recurring components of FIGS. 1 to 8.

With reference to the drawings, like or functionally equivalent elements are provided with like reference numerals in the drawings, only the reference numerals required for understanding the drawing, including in context with the other drawings, being used in each case. Therefore, doubled-up reference numerals in like or similar components of a drawing are largely omitted. Recurring components of FIGS. 1 to 8 are summarised in FIG. 9 and are therefore not additionally explained.

FIG. 1 illustrates the basic mode of operation of the method and device by way of a schematic embodiment. The reaction mixture 2 is located in a shaken reactor 1. Light 17 is shone into the reactor 1 and the reaction mixture 2 from at least one light source 4. The shone-in light 17 interacts with at least one component of the reaction mixture 2, and leaves said mixture and the reactor 1 again, in particular but not exclusively as backscattered light 18 and/or as forward-scattered or transmitted light 19. The light 18/19 exiting the reaction mixture 2 thereupon interacts with at least one light sensor 5/6, which converts the detected light intensity into an analogue electrical signal. This is in turn digitised by an evaluation and control unit 8 belonging to at least one light sensor 5/6, and stored as a measurement value 20/21 and/or passed to at least one processor 9. The firmware 30 running on the processor 9 controls the measurement value detection, in particular but not exclusively in terms of the measurement frequency, the sensor sensitivity, and the amplification of the analogue measurement signal. In addition, the firmware 30 running on the processor 9 controls the radiation intensity of the light source 4 by way of the light source control unit 7.

Both the light source 4 and the light sensor 5/6 can be equipped with optics. The optics 38 modify the light 17 emitted by at least one light source 4 and shone into the reactor 1 and reaction mixture 2, whilst the optics 39 modify the light 18/19 emitted by the reactor 1 and reaction mixture 2, which is thereupon detected by at least one light sensor 5/6. The components useable for the optics 38 and 39 comprise, in particular but not exclusively, optical filters, lenses, lens systems, apertures, aperture systems, optical gaps and shutters, polarisers, half-wave and quarter-wave plates, diffraction gratings, prisms and optical fibres. In some embodiments, the optics 38/39 can be controlled by processors 9 comprising firmware 30.

The processor 9 and firmware 30 communicate with a more powerful processor 10 (for example a PC) and the user software 31 running thereon via at least one radio module 28 or at least one wired communication module 29 or even directly. This communication includes, in particular but not exclusively, the transmission of measurement and analysis data and other information, such as control commands for components of the device which are controlled by the processor 9, firmware and/or software parameters, time and clock signals, firmware updates and license information.

A plurality of measurement data detected sequentially in a particular time interval and at a particular measurement frequency are combined into a series of measurements 34 by the firmware 30 on the processor 9 and/or the user software 31 on the processor 10. Processing a series of measurements 34 using suitable mathematical and computing methods and algorithms 36 subsequently provides at least one parameter and/or at least one property 37 of the overall process running in the reaction mixture 2. Suitable mathematical and computing methods and algorithms 36 may be implemented both in firmware 30 and in user software 31. In an advantageous embodiment of the invention, and also as is shown in FIG. 1, the majority of the methods and algorithms 36 used are implemented and run by the user software 31, since the computing power of the processor 10 is usually much higher and thus better suited to more complex methods and algorithms 36 than that of the processor 9.

Measurement signals 20/21, series of measurements 34 and process parameters/properties 37 determined at various moments can be combined by the processor 9 comprising firmware 30 and/or the processor 10 comprising user software 31 into at least one time series 35 of the relevant data type. Processing a time series 35 using suitable mathematical and computing methods and algorithms 36 subsequently provides at least one further parameter and/or at least one further property 37 of the overall process running in the reaction mixture 2.

On the basis of at least one type of data determined from the optical measurements during the process sequence (process parameters/properties 37, time series 35, series of measurements 34, measurement signals 20/21), automated intervention in the reaction sequence of the reaction mixture 2 in the reactor 1 is possible during the process. For this purpose, substances are added to the reaction mixture 2 via a metering system 12. In addition, by way of a temperature control system 25, the temperature of the reactor 1 and the reaction mixture 2 can be set so as to influence the current process in a targeted manner.

Figure 2:
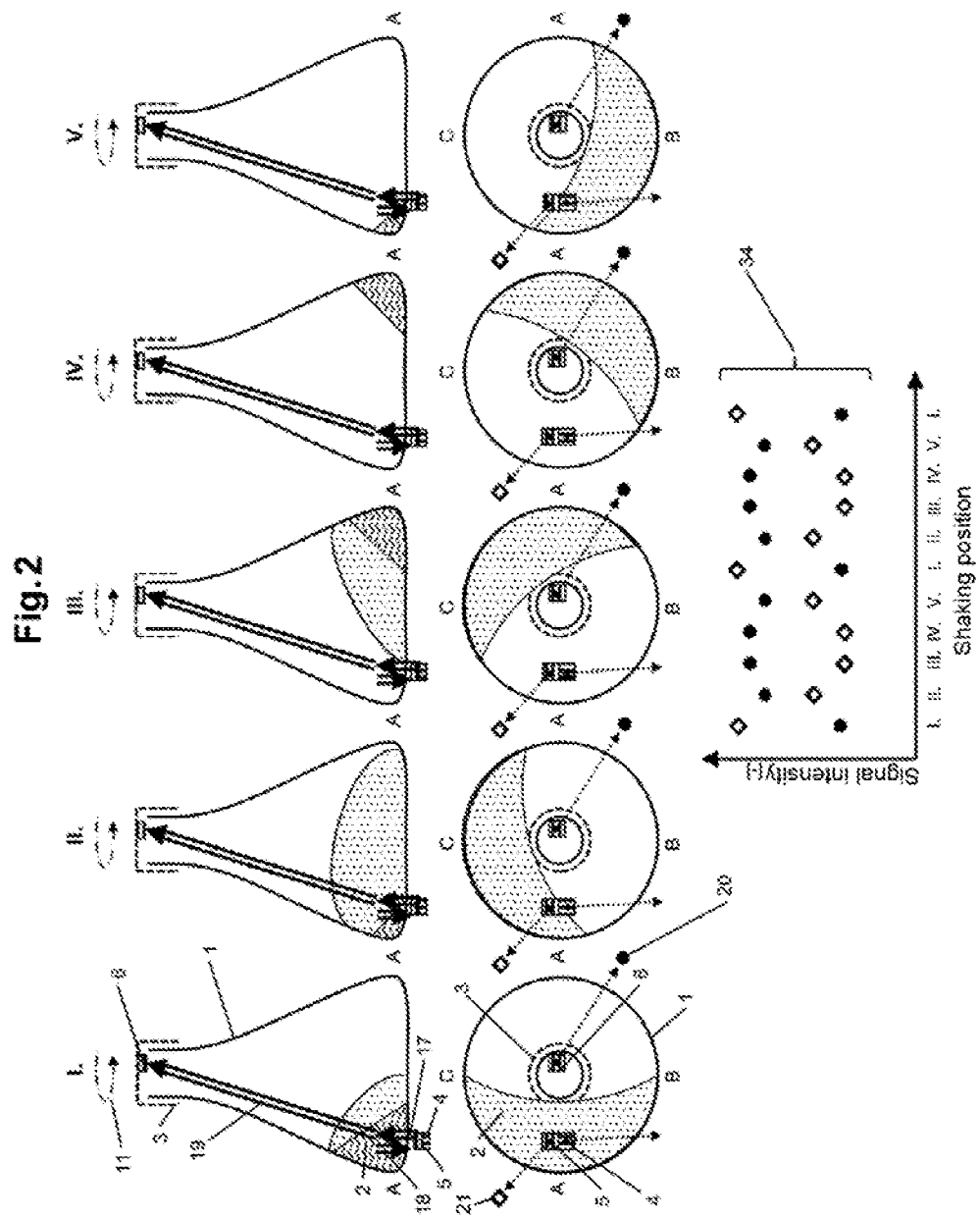
FIG. 2 shows by way of example, for a reactor 1 under orbital shaking, the dependency of the measured light intensities on the shape and distribution of the reaction mixture 2 in the reactor 1.

FIG. 2 and FIG. 3 illustrate the functional principle of the method and device using the example of a flask under orbital shaking as a reactor 1 (FIG. 2) and using the example of a general reactor 1 under rocker shaking (FIG. 3). In the two embodiments shown, a light source 4, which shines light 17 into the reactor 1 and into the reaction mixture 2, is located below the reactor 1 and the reaction mixture 2. A light sensor 5 for detecting backscattered light 18 is also located below the reactor 1 and the reaction mixture 2. A light sensor 6 for detecting transmitted and forward-scattered light 19 is placed above the reactor 1 and the reaction mixture 2. The light sensor 5 provides the scattering signal 21, and the light sensor 6 provides the transmission signal 20.

FIG. 2 and FIG. 3 each show five example shaking positions (I. to V.), the distribution of the reaction mixture 2 in the reactor 1 being selected schematically to illustrate the functional principle of the invention. Neither of the drawings shows actually taken measurement results. For better illustration of the distribution of the reaction mixture 2 in the reactor 1, both a lateral section and a view from below are shown for the flask under orbital shaking in FIG. 2. The lateral section is made, projecting from the plane of the drawing, along the line A-A of the view from below, in such a way that the view of the observer extends along the line B-C. By contrast, FIG. 3 is merely a lateral section.

In the flask under orbital shaking in FIG. 2, during shaking, a characteristic distribution of the reaction mixture 2 in the reactor 1 occurs, the rotation of the reaction mixture 2 in the reactor 1 resulting in the height of the fill level above the light source 4 and light sensor 5, and thus also the height of the fill level between the light source 4 and light sensor 6, continuously changing periodically. For a constant wavelength and intensity of the shone-in light 17, for constant external light, under the assumption of a constant optical density of the reaction mixture 2 and in the absence of inhomogeneities such as bubbles or agglomerates of reaction mixture components, the transmission signal 20 and the scattering signal 21 are each a function of the fill level of the reaction mixture 2 in the reactor 1 brought about by the distribution. A detail from the correspondingly periodic signal progression is shown schematically in the graph in FIG. 2.

When the fill level above the light source 4 and light sensor 5 is at a maximum (FIG. 2, shaking position I.), the scattering signal 21 of light sensor 5 is also at a maximum, whilst the transmission signal 20 of light sensor 6 is at a minimum, since in this case the smallest fraction of the light passes through the reaction mixture by comparison with the other shaking positions. At lower fill levels above the light source 4 and light sensor 5 which are brought about by the movement of the reaction mixture 2 in the reactor 1, the scattering signal 21 of light sensor 5 is correspondingly lower and the transmission signal 20 of light sensor 6 is correspondingly higher than in shaking position I. When there is no reaction mixture above the light source 4 and light sensor 5, the scattering signal 21 of light sensor 5 is at a minimum, and the transmission signal 20 of light sensor 6 is at a maximum (FIG. 2, shaking positions III. and IV.).

The signal progressions of a reactor under rocker shaking turn out analogously in FIG. 3. When the fill level above the light source 4 and light sensor 5 is at a maximum (FIG. 3, shaking position I.), the scattering signal 21 of light sensor 5 is also at a maximum, whilst the transmission signal 20 of light sensor 6 is at a minimum. When there is no or almost no reaction mixture above the light source 4 and light sensor 5, the scattering signal 21 of light sensor 5 is at a minimum and the transmission signal 20 of light sensor 6 is at a maximum (FIG. 3, shaking position V.).

All of the signals 20 and 21 recorded at an optical density which is sufficiently constant for measuring purposes can be combined into series of measurements 34, which can be used in accordance with the explanations for FIG. 1 to determine the optical density and/or the change in the optical density of the reaction mixture 2 and to determine further process parameters and process properties. As a result of the periodicity within a series of measurements 34, outliers caused by disturbing factors in the curve progression can be efficiently identified and eliminated, greatly increasing the reliability of the determination of the optical density and further process parameters and process properties.

In addition, from the form of these series of measurements 34, qualitative and quantitative conclusions regarding fluid-mechanical parameters and properties of the reaction mixture 2 can be reached, since the shape and distribution of the reaction mixture 2 in the reactor 1 and thus the measurement signals 20/21 within a series of measurements 34 are dependent on the fluid-mechanical parameters and properties of the reaction mixture 2. One fluid-mechanical parameter of significance to the process is the viscosity of the reaction mixture 2, which can greatly affect the shape and distribution thereof in the reactor 1. The invention therefore makes it possible, on the basis of the measurement method thereof, to assess the viscosity of the reaction mixture 2, and this is of great value for monitoring and optimising a wide range of biotechnological and chemical processes in which the viscosity changes during the process (for example as a result of cell growth, filamentous growth, formation of gel-forming substances, formation of polymers, etc.).

Figure 4:
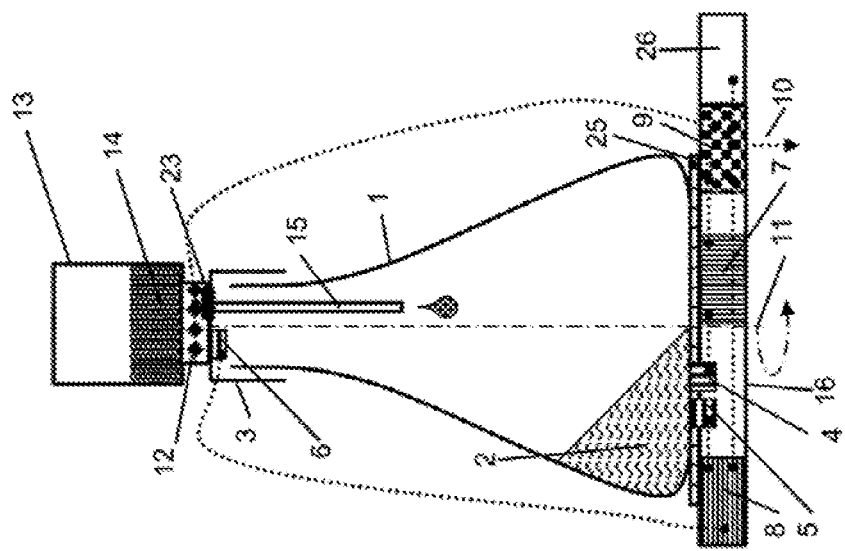
FIG. 4 shows an embodiment of the device for shaking flasks under orbital shaking.

FIG. 4 shows an embodiment of the device for carrying out the method of the invention for shaking flasks under orbital shaking. In this case, a typical Erlenmeyer flask is used as a reactor 1, which contains the reaction mixture 2 and can be clamped together with the housing 16 placed below it in a commercially available clamping device or a holder. In the housing 16 there is a light source 4 along with a control unit 7, a light sensor 5 having an evaluation and control unit 8, and a processor 9 connected to the control units 7/8. The processor 9, which in an advantageous embodiment of the invention is formed by a microprocessor, is connected to a storage battery 26 to provide electrical power. This also applies to all of the other electronic components of the device; however, for reasons of clarity, the corresponding connections are not shown. Further, a temperature control system 25, consisting for example of a temperature sensor, a Peltier element and a control unit, is connected to the processor 9.

A second part of the device in FIG. 4 is attached to the cover 3 of the reactor 1. For detecting transmitted and/or forward-scattered light, there is a light sensor 6 in the cover (optionally behind a glass or plastics material plate for reasons of sterility), which, like the light sensor 5 placed on the underside of the flask, is connected to the evaluation and control unit 8. On the cover, there is an electronic metering system 12, which is connected to the processor 9 and, under the control thereof, can pass a component 14 from the reservoir 13 via a supply line 15 into the reactor 1 and the reaction mixture 2. The opening around the supply line 15 is sealed in a sterile manner by a septum 23.

Figure 5:
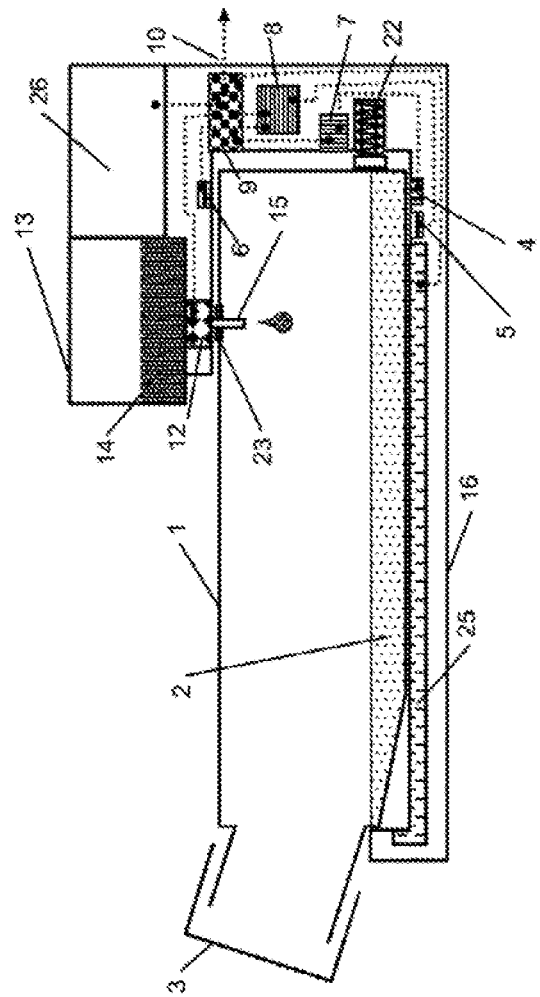
FIG. 5 shows an embodiment of the device for T-flasks under rocker or orbital shaking.

FIG. 5 shows an embodiment of the device for carrying out the method of the invention for culture flasks (T-flasks) under rocker or orbital shaking. In this case, the reactor 1 is formed by a T-flask which is filled with a reaction mixture 2 and which is fixed to the housing 16 by means of a clamping device 22. Analogously to FIG. 4, in the housing 16 there is a light source 4 along with a control unit 7, two opposite light sensors 5/6 having an evaluation and control unit 8, a processor 9 connected to the control units 7/8, and an electronic metering system 12, which is also connected to the processor 9 and, under the control thereof, can pass a component 14 from the reservoir 13 via a supply line 15 which penetrates through the septum 23 into the reactor 1 and the reaction mixture 2. The processor 9, which in an advantageous embodiment of the invention is formed by a microprocessor, is connected to a storage battery 26 to provide electrical power. This also applies to all of the other electronic components of the device; however, for reasons of clarity, the corresponding connections are not shown. Further, a temperature control system 25, attached below the reactor 1 and consisting for example of a temperature sensor, a Peltier element and a control unit, is connected to the processor 9.

Figure 7:
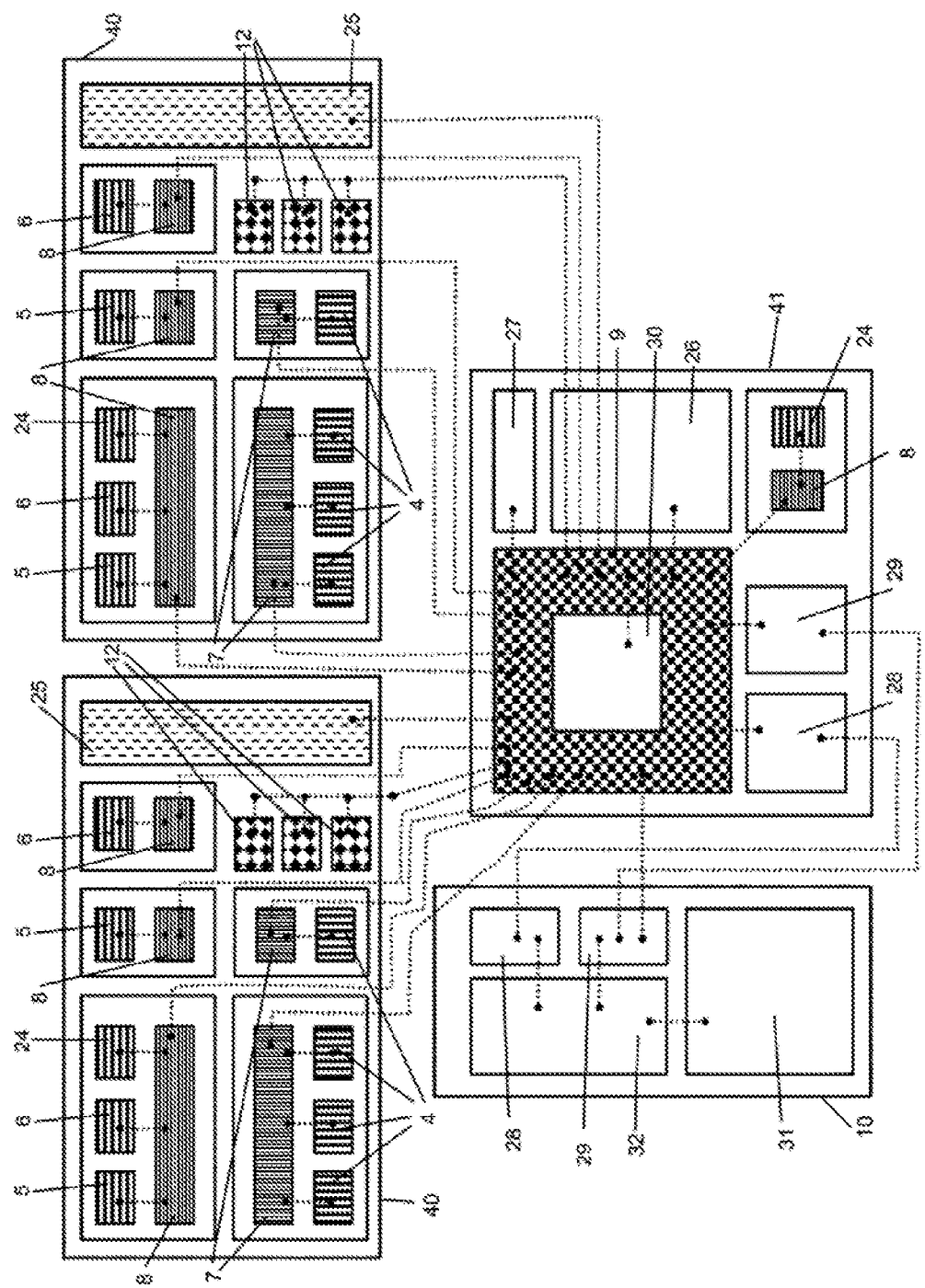
FIG. 7 is a schematic drawing of a modular embodiment of the device.

The embodiments of the invention shown in FIG. 4 and FIG. 5 are non-modular and are functional individually in combination with a processor 10 comprising user software 31. However, it may be advantageous to modularise the device. In this regard, FIG. 6 is a schematic drawing of a non-modular embodiment of the device, and FIG. 7 is a schematic drawing of a modular embodiment of the device, so as to describe in more detail the interaction and modularisability of the individual device components. The schematically shown electronic device components form functional units, which need not necessarily be in the form of individual electronic or other technical components. In some cases, a plurality of functional units can be combined in one electronic component (for example on a chip).

The non-modular embodiment shown in FIG. 6 consists of two primary components, a measuring station 40 and a processor 10 comprising user software 31, the measuring station further comprising, in addition to the functional units (4/5/6/7/8/24) relevant for measurements and the units (12/25) which affect the reaction mixture 2, a processor 9 comprising firmware 30 and, depending on the embodiment, various communication modules 28/29 and the electrical power supply 26/27. However, to carry out the parallelisation which is desired in most shaken reactor applications, it may be advantageous to keep each measuring station 40 which is in direct contact with a reactor 1 as small as possible. The modularised embodiment in FIG. 7 makes this possible by transferring some functional units out of the measuring stations 40 into a base station 41, which can be jointly used by a plurality of measuring stations 40, and by restricting each measuring station 40 to the functional units absolutely required at the reactor 1.

As is shown in FIG. 7, in particular the processor 9 comprising firmware 30 and the electrical power supply can be integrated into a base station 41 jointly used by a plurality of measuring stations 40, by way of a storage battery 26 or a mains connection 27 and the communication modules 28/29 potentially required for communication with the processor 10 and the user software 31. Each measuring station 40 is connected to the base station 41 to provide power and for communication, the communication between the processor 9 comprising firmware 30 and the functional units of the measuring station (including in the non-modular construction) taking place using serial communication protocols and standards (for example SPI, I$^2$C, USB, CAN, Ethernet, IEEE 802 standards etc.) in an advantageous embodiment of the invention.

The following statements apply both to non-modular (for example FIG. 6) and to modular (for example FIG. 7) embodiments of the invention.

The functional units communicating with the processor 9 and the firmware 30 are, in particular but not exclusively, the control unit 7 for at least one light source 4 and the control and evaluation unit 8 for at least one light sensor 5/6, it also being possible for a measuring station 40 to contain a plurality of control/evaluation units 7/8 and a plurality of light sources 4 and light sensors 5/6. The primary components of the control unit 7 for at least one light source 4 may, in particular but not exclusively, be digital potentiometers, diode drivers, laser drivers and microprocessors, which can be used to modify and set properties such as the intensity or spectral ranges of the light 17 emitted by the light source 4.

The purpose of the control and evaluation unit 8 for at least one light sensor 5/6 is to digitise the analogue measurement signals generated by the light sensor 5/6, to amplify and filter the analogue measurement signals generated by the light sensor 5/6 prior to digitisation, and to pass on the digitised measurement data to the processor 9 and the firmware 30. Primary components of the control and evaluation unit 8 for at least one light sensor 5/6 may be, in particular but not exclusively, digital potentiometers, operational amplifiers, analogue-digital converters, suitable frequency filters and microprocessors.

In some embodiments, light sources 4 and light sensors 5/6 may be displaceable individually or jointly or jointly with the associated control/evaluation unit 7/8, and this can be carried out, in particular but not exclusively, by electric motors controlled by the processor 9 comprising firmware 30 or other electrical magnet systems. The purpose of the displaceability is to adapt the positions of light sources 4 and light sensors 5/6 so as to adapt the device to the relevant process and measurement requirements in an automated manner.

Further, if required, at least one temperature control system 25 and at least one metering system 12 may be integrated into the measuring station, which are both controlled by way of the processor 9 comprising firmware 30 so as to intervene in the process with feedback to the measurement data and the further parameters and properties of the process determined by the processor 10 and user software 31. Primary components of the temperature control system 25 may be, in particular but not exclusively, temperature sensors, Peltier elements, analogue-digital converters and microprocessors. Primary components of the metering system 12 may be, in particular but not exclusively, electrically controllable valves and pumps, temperature sensors, liquid sensors, pressure sensors, Peltier elements, analogue-digital converters and microprocessors.

Both in at least one measuring station 40 and in at least one base station 41, at least one ambient light sensor 24 comprising a corresponding control and evaluation unit 8 may be integrated so as to detect effects on the optical measurements on the reactor(s) 1 and the reaction mixture(s) 2 and be able to eliminate or reduce corresponding interferences in the measurement data.

In an advantageous embodiment of the invention, the communication between the processor 10 and the user software 31 and the processor 9 comprising firmware 30 also takes place using serial communication protocols and standards (for example SPI, I²C, USB, CAN, Ethernet, IEEE 802 standards etc.) Any communication modules 28/29 required for this purpose are located on the processor 10 and on the processor 9 of the measuring station 40 or base station 41, depending on the embodiment.

In an advantageous embodiment of the invention, the hardware 32 of the processor 10 is much more powerful than the processor 9, in such a way that much more complex and more resource-intensive mathematical methods and computing algorithms can be implemented in the user software 31 than in the firmware 30, which is primarily for controlling the electronic components on the measuring station and/or base station 40/41.

Figure 8:
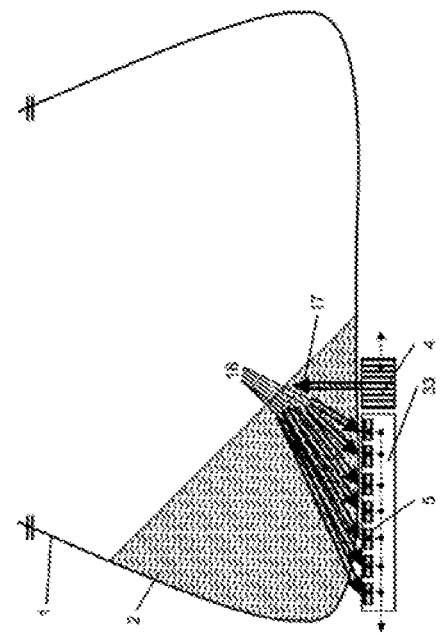
FIG. 8 schematically shows the use of a sensor array as a light sensor 5.

FIG. 8 illustrates the use of sensor arrays as light sensors 5/6 using the example of a flask under orbital shaking as a reactor 1. The light 17 shone into the reactor 1 and the reaction mixture 2 by a light source 4 is scattered on at least one component of the reaction mixture 2. The scattering is continuous over a particular scattering angle range, but usually in all spatial directions. The intensity of the scattered light 18 is dependent on the scattering angle. This dependency can be exploited so as to take very exact and reliable measurements in a wide range, covering several orders of magnitude, of the optical density of the reaction mixture 2. For this purpose, many individual light sensors 5 are combined into a light sensor array 33, which simultaneously detects the scattered light intensity at various scattering angles. The comparison and the correlation of the angle-dependent scattered light intensities recorded at different times ensure reliable measurements over several orders of magnitude of the optical density. This reliability can be achieved, in particular but not exclusively, by targeted selection of the optimum light sensor 5 in the light sensor array 33 in each case and by comparing and weighting the values of all of the light sensors 5 in the light sensor array 33 by suitable mathematical methods. Light sensor arrays 33 of this type may also be used as transmission sensors, in particular but not exclusively so as to detect the transmission in different spatial directions simultaneously.

In particular but not exclusively, integrated one-dimensional and two-dimensional light sensor arrays, such as CCD chips or CMOS APS chips, and other one-dimensional and two-dimensional arrays of photodiodes, photoresistors and phototransistors may be used as a light sensor array 33.

FIGS. 10 to 14 show example measurement results which were determined by the method according to the invention. The measurements were taken using a device according to FIG. 2 in Erlenmeyer flasks, under orbital shaking at 160 revolutions per minute, as a reactor 1. Suspensions of baker's yeast cells (*S. cerevisiae*) in LB medium were used as a reaction mixture 2, relative flask fill volumes of 20% being used for the measurements of FIGS. 10 to 12 and relative flask fill volumes of 10% being used for the measurements of FIGS. 13 to 14. An LED having a peak wavelength of 528 nm was used as a light source 4, and was placed non-centrally below the flask (similarly to FIG. 2). Photodiodes were used as light sensors 5/6, a photodiode being placed below the flask next to the light source 4 as a light sensor 5 for scattered light and a photodiode being placed in the cover 3 of the flask as a light sensor 6 for transmitted light in each case. The light intensity $I_0$ before traversing the reactor and the reaction mixture was not measured. The formulae and equations cited in the following, in particular in reference to FIGS. 10 to 14, for the relationships between biomass concentration and signal intensities or other results of optical measurements apply in an identical or modified form to many other components of possible reaction mixtures 2 which interact with shone-in light 17, in particular but not exclusively to concentrations of organisms, proteins, nucleic acids (for example DNA, RNA), lipids, sugars, biopolymers, plastics materials, and other organic and/or inorganic particles, molecules, ions and, generally, substances.

FIG. 10 illustrates the correlation between the intensity of the signal of the light sensors 5/6 and the biomass concentration in the reaction mixture 2. In each case, a signal intensity value represents the average of a series of transmission or scattering measurements 34/20 or 34/21, as shown by way of example in FIG. 11 for the signal intensities from FIG. 10 at biomass concentrations of 0.33 g/l, 0.99 g/l and 2.04 g/l. As a result of the detection according to the invention of the light by the light sensors at a frequency such that the shaking frequency is not an integer multiple of the detection frequency, according to the invention the periodically fluctuating fill level results in a sensor signal which fluctuates periodically as a result of the shaking. For the example measurement shown in FIG. 10-13, a measurement frequency of 200 Hz was selected, in such a way that a shaking period is represented by 75 measurement points.

A clear relationship between the signal intensity determined as the average of a series of measurements and the biomass concentration of the reaction mixture can be seen from FIG. 10, both for the transmission values and for the scattering values. In the measurement range shown, the represented signal intensities of the transmission and scattering light are each in an exponential relationship with the biomass concentration, as is also generally known for the absorption of light in homogeneous diluted solutions. The corresponding Beer-Lambert law for the transmission of light is $$E = \log_{10}\left(\frac{I_0}{I}\right) = \varepsilon \cdot c \cdot d$$

where E is the optical density, $I_0$ is the light intensity before traversing the medium, I is the light intensity after traversing the medium, ε is the extinction coefficient, c is the concentration of the absorbing component, and d is the distance traversed by the light, which in this case is formed by the (optionally weighted) average of all of the light distances as a result of the periodic light distance fluctuations according to the invention.

Figure 12:
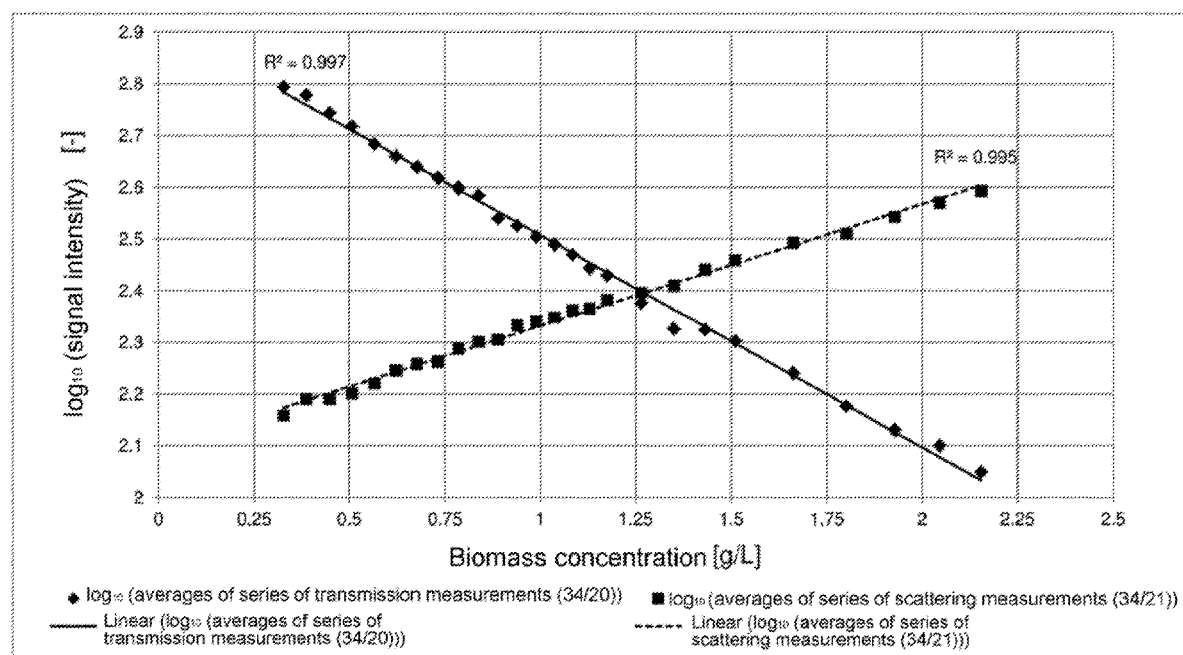

The linear relationship between the optical density and the absorbing component of the reaction mixture also applies to the logarithm of the signal intensities and the biomass, as can be seen from FIG. 12, since it can be assumed that $I_0$ is constant for all measurements within an experiment. If $I_0$ is unknown, not only the change in the optical density and the biomass concentration can be determined from the changes in the signal intensity, but also the absolute biomass concentration, if the biomass concentration for one signal intensity value is known. For transmission signals, this results from the difference in the optical densities and the rearrangement of the Beer-Lambert law.

$$\Delta E = E_2 - E_1 = \log_{10}\left(\frac{I_1}{I_2}\right) = \varepsilon \cdot d \cdot (c_2 - c_1)$$

$$c_2 = \frac{\log_{10}\left(\frac{I_1}{I_2}\right)}{\varepsilon \cdot d} + c_1$$

To determine absolute biomass concentrations in this manner, E the extinction coefficient and d the distance traversed by the light must be known, and can be determined from calibration series. If E and d are unknown, absolute biomass concentrations can still be determined if the biomass concentration for one signal intensity value is known and if $I_0$ is known (in particular but not exclusively in that $I_0$ is determined during the experiment, or in that required $I_0$ values are determined by the product manufacturer and stored in the appliance). This results from the change in the relative biomass concentration $c_2/c_1$.

$$\frac{c_2}{c_1} = \frac{\frac{\log_{10}\left(\frac{I_1}{I_2}\right)}{\varepsilon \cdot d} + c_1}{c_1} =$$

$$\frac{\log_{10}\left(\frac{I_1}{I_2}\right)}{\varepsilon \cdot d} \cdot \frac{1}{c_1} + 1 = \frac{\log_{10}\left(\frac{I_1}{I_2}\right)}{\varepsilon \cdot d} \cdot \frac{\varepsilon \cdot d}{\log_{10}\left(\frac{I_0}{I_1}\right)} + 1 = \frac{\log_{10}\left(\frac{I_1}{I_2}\right)}{\log_{10}\left(\frac{I_0}{I_1}\right)} + 1$$

$$c_2 = \left(\frac{\log_{10}\left(\frac{I_1}{I_2}\right)}{\log_{10}\left(\frac{I_0}{I_1}\right)} + 1\right) \cdot c_1$$

The Beer-Lambert law cannot be used to determine the biomass concentration from scattering signals. However, as can be seen from FIG. 10/12, the dependency between the scattering signal and the biomass concentration can also be modelled exponentially in the shown measurement range, in such a way that, analogously to the above equations, the scattering intensity $I_s$ can be expressed as $$I_s = I_0 \cdot 10^{\sigma \cdot c \cdot V}$$

where $I_0$ is the light intensity before traversing the medium, $\sigma$ is the scattering coefficient, c is the concentration of the scattering component, and V is the reaction volume generating detectable scattered light, which in this case, because of the periodic light distance fluctuations according to the invention, is taken as the (optionally weighted) average of all values of V. As a result of multiple scattering, the light detected by a scattered light sensor 5 does not necessarily originate from the entire volume traversed by the light. Rather, the reaction volume V generating detectable scattered light is dependent on the relevant biomass concentration, in particular at higher biomass concentrations, in such a way that overall, for corresponding measurement conditions, there is a linearly approximable relationship between the scattering intensity I and the biomass concentration, which can be expressed as $$I_s = I_0 \cdot \sigma_{lin} \cdot c$$

where $I_0$ is the light intensity before traversing the medium, $\sigma_{lin}$ is the linear scattering coefficient, and c is the concentration of the scattering component. At low biomass concentrations, analogously to the transmission measurement, the biomass concentration is $$c_2 = \frac{\log_{10}\left(\frac{I_{s2}}{I_{s1}}\right)}{\sigma \cdot V} + c_1$$

or $$c_2 = \left(\frac{\log_{10}\left(\frac{I_{s2}}{I_{s1}}\right)}{\log_{10}\left(\frac{I_{s1}}{I_0}\right)} + 1\right) \cdot c_1$$

For higher biomass concentrations, the biomass concentration can be approximated as $$c = \frac{I_s}{I_0 \cdot \sigma_{lin}}$$

$$c_2 = \frac{I_{s2}}{I_{s1}} \cdot c_1$$

Figure 13:
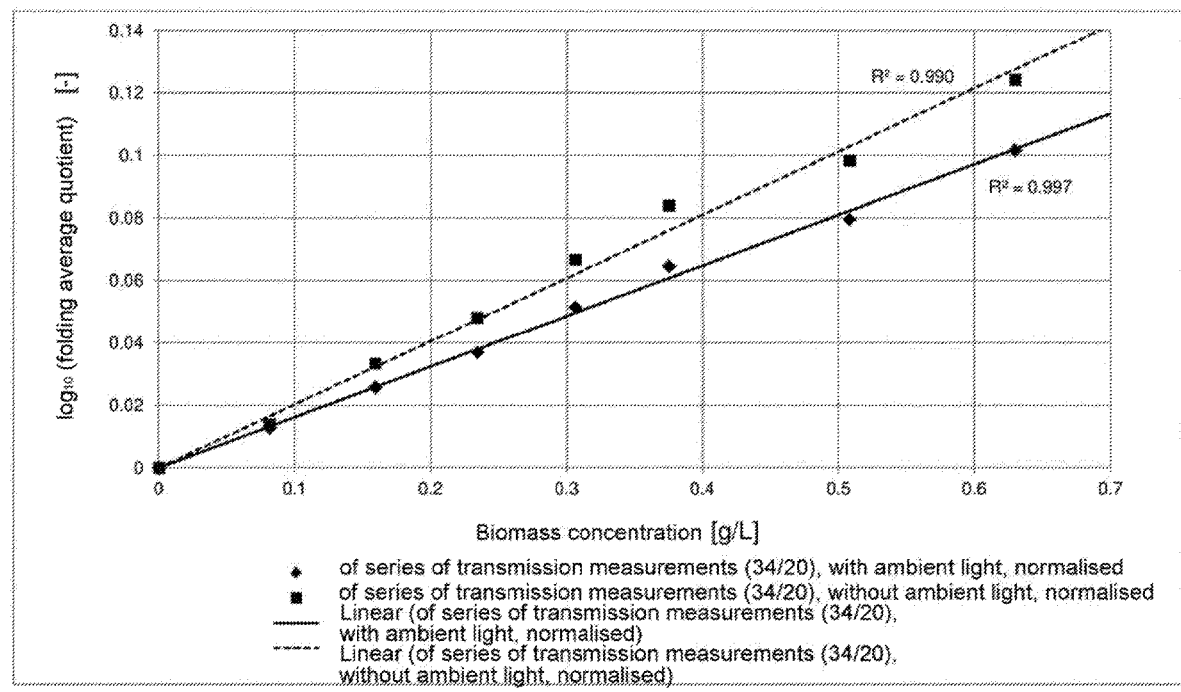

For correct evaluation of the series of measurements 34 which fluctuate periodically according to the invention, further mathematical methods are available in addition to the method of averaging applied above, in particular but not exclusively direct fitting of periodic model functions to the series of measurements 34 or statistical evaluations of each series of measurement 34 using classifications, fitting of distribution functions, correlation analyses between different measurement series of a light sensor 5/6 and/or different light sensors 5/6 etc. A further mathematical method, which is suitable in particular for robust evaluation of the series of measurements at low biomass concentrations, is discrete folding of two series of measurements determined at different moments, which in each case results in a discrete folding function F for the folded pair of measurement series. This folding function can now be mathematically evaluated further and correlated with the biomass. One possible type of evaluation involves taking the average of all of the elements of a discrete folding function. For transmission measurements, FIG. 13 shows the correlation between the base-ten logarithm of the quotients of the folding averages and the biomass concentration. Analogously to the above statements on the evaluation of the series of transmission measurements, this relationship is in accordance with the equation $$\Delta E_F = \log_{10}\left(\frac{F_1}{F_2}\right) = \varepsilon_F \cdot d \cdot (c_2 - c_1)$$

where $\Delta E_F$ is the change in the folding-specific optical density, $\overline{F}_1$ and $\overline{F}_2$ are the averages of the folding functions $F_1$ and $F_2$, $\varepsilon_F$ is the folding-specific extinction coefficient, c is the concentration of the absorbing component, and d is the distance traversed by the light. If there is at least one known concentration value, this results in a biomass concentration of $$c_2 = \frac{\log_{10}\left(\frac{\overline{F}_1}{\overline{F}_2}\right)}{\varepsilon_F \cdot d} + c_1$$

FIG. 13 further shows that the invention makes robust measurements possible both in the exclusion of and in the presence of ambient light (in particular daylight and room lighting) even in low biomass concentration ranges. The measurement data under ambient light were recorded in daylight and additional room lighting, whilst the measurements without ambient light were taken by darkening the entire measurement construction using a black, opaque fabric. Both measurements show a linear relationship between biomass concentration and the base-ten logarithm of the folding average quotients even at low biomass concentrations (the linear relationship also applies to the signal averages which are not shown). Only the gradient of the linear functions is different; under ambient light, the processed signal increases more slowly, since the level of the periodic fluctuations according to the invention in the transmission signal 20 turns out lower than for the darkened measurement as a result of the higher background light intensity. However, the gradient can be appropriately scaled to the ambient light conditions by using at least one ambient light sensor 24 which is read in parallel with the measurement on the reactor 1 and reaction mixture 2, in such a way that robust measurements are possible even in varying ambient light.

Figure 14:
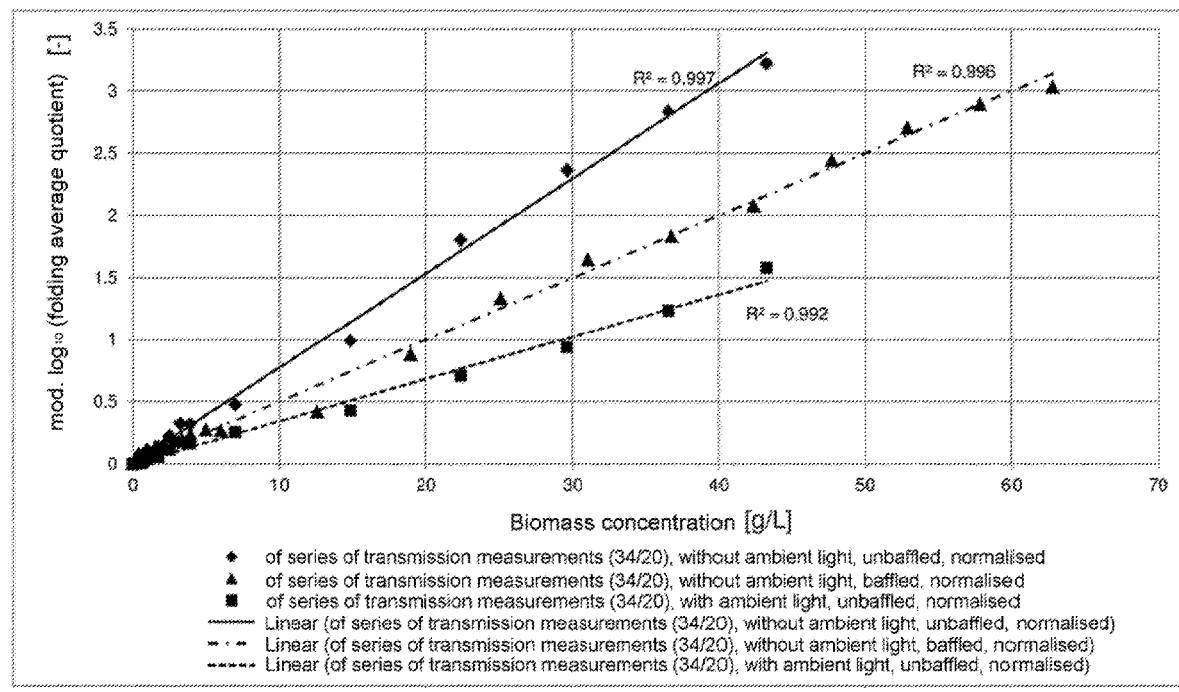

FIG. 14 shows the relationship between biomass concentration and a modified base-ten logarithm of the folding average quotients of series of transmission measurements over a wide range of concentrations up to more than 40 g/l. Results are shown for two measurements on unbaffled flasks, one measurement each with and without ambient light, and a measurement on a baffled flask without ambient light. The measurement frequency on the unbaffled flask was 200 Hz, whereas series of measurements for the baffled flask were recorded at 450 Hz so as to be better able to detect the turbulent distribution of the reaction mixture 2 in the reactor 1.

Over the biomass concentration range shown in FIG. 14, the relationship between the transmission intensity and the biomass concentration can no longer be modelled using a simple exponential function, and so the Beer-Lambert law is no longer valid, and has to be modified. This relationship can be optimally described using the sum of at least two exponential functions having different coefficients in the exponent, for example $$I = I_0 \cdot (a \cdot 10^{-\varepsilon_1 \cdot c \cdot d} + b \cdot 10^{-\varepsilon_2 \cdot c \cdot d})$$

Since functions of this type usually cannot be solved analytically for the concentration c, the biomass concentration has to be determined using an analytically solvable approximation function which sufficiently accurately represents the progression of the sum of a plurality of exponential functions. For this purpose, the function on which the Beer-Lambert law is based can for example be modified to $$I = I_0 \cdot 10^{-\varepsilon \cdot c^z \cdot d}$$

resulting in a biomass concentration c of $$c = \sqrt[z]{\frac{\log_{10}\left(\frac{I_0}{I}\right)}{\varepsilon_z \cdot d}}$$

where $I_0$ is the light intensity of the medium, I is the light intensity after traversing the medium, $\varepsilon_z$ is the corrected extinction coefficient, z is the correction exponent and d is the distance traversed by the light. Analogously to the above equations for the transmission, the biomass concentration can subsequently also be calculated as $$c_2 = \sqrt[z]{\frac{\log_{10}\left(\frac{I_1}{I_2}\right)}{\varepsilon_z \cdot d} + c_1^z}$$

As was shown for the above example measurement, the folding averages can also be used for the intensities and the corrected folding-specific extinction coefficients can also be used for the corrected extinction coefficients. The application of a Beer-Lambert law modified in this manner makes it possible to determine the biomass concentration over a wide measurement range exclusively by using transmission data. By way of a suitable combination of the measurement data of a plurality of light sensors 5/6, the robustness and exactness of the measurements can additionally be improved.

FIG. 14 additionally demonstrates how the invention can be used on continuously shaken baffled systems, which are characterised by turbulent flows, inhomogeneous reaction mixture distributions in the reactor, and disrupting factors such as bubbles and foam. The technologies known in the art cannot take robust measurements on systems of this type during shaking operation. This is only possible by recording, according to the invention, a multiplicity of measurement values, at a frequency such that the shaking frequency is not an integer multiple of the detection frequency.

LIST OF REFERENCE NUMERALS

1 Reactor
2 Reaction mixture
3 Cover
4 Light source
5 Light sensor for scattered light
6 Light sensor for transmitted and/or forward-scattered light
7 Control unit for at least one light source 4
8 Evaluation and control unit for at least one light sensor 5/6
9 Processor (for example comprising central control unit as a microcontroller or SoC)
10 Processor (for example in the form of a PC or server)
11 Shaking axis orthogonal to the shaking plane in orbital shaking
12 Metering system
13 Reservoir
14 Component to be added
15 Supply line
16 Housing
17 Beam of light emitted by light source
18 Beam of backscattered light
19 Beam of transmitted and/or forward-scattered light 20 Signal of 6 ("transmission signal")
21 Signal of 5 ("scattering signal")
22 Clamping device
23 Septum
24 Ambient light sensor
25 Temperature control system
26 Storage battery
27 Mains-connected power supply
28 Radio module
29 Wired communication module
30 Firmware
31 User software comprising graphical interface
32 Processor hardware
33 Light sensor array
34 Series of measurements
35 Time series
36 Mathematical and/or computing methods/algorithms
37 Parameters and properties of the process
38 Optics for modifying the light of light source 4
39 Optics for modifying the light from the reaction mixture 2 and reactor 1
40 Measuring station
41 Base station

What is claimed is:

1. A method for determining the optical density and/or the change in the optical density of a reaction mixture in a shaken reactor, comprising the following steps:
    providing light from at least one light source along a light path that enters the reaction mixture,
    detecting the light transmitted entirely through the reaction mixture and scattered from the reaction mixture in the light path by at least one light sensor,
    shaking the reactor and the reaction mixture during the detection of the light by the at least one light sensor, wherein the light detected by the at least one light sensor is at a frequency such that the shaking frequency is not an integer multiple of the detection frequency, and
    combining at least two measurement points detected by the at least one light sensor in a particular time interval into a series of measurements.

2. The method according to claim 1, characterized in that:
    the light is detected by the at least one light sensor at a frequency higher than the shaking frequency, and/or
    at least one light path of at least one light source/light sensor pair is orientated non-parallel to a shaking axis and/or shaking plane, and/or
    there is no relative movement between the reactor and at least one light sensor.

3. The method according to claim 1, characterized in that, from at least one series of measurements determined in a particular time interval, the optical density and/or the change in the optical density and/or at least one fluid-mechanical parameter and/or at least one fluid-mechanical property of the reaction mixture in the measured time interval is determined by means of at least one suitable mathematical/computing method and/or at least one model function.

4. The method according to claim 1, characterized in that, from at least one series of measurements and/or at least one time series of a parameter of the reaction mixture determined from at least one measurement point and/or at least one series of measurements, at least one further parameter of the reaction mixture is determined by means of at least one suitable mathematical/computing method and/or at least one model function.

5. The method according to claim 1, characterized in that at least one model function is generated afresh and/or modified using at least one suitable mathematical method and/or at least one suitable computing algorithm.

6. The method according to claim 1, further comprising the steps of:
    controlling at least one metering system for adding at least one substance as a function of the optical density and/or of the change in the optical density and/or of at least one other process parameter, and/or
    operating at least one further technical system which affects the process, in particular a system for temperature-controlling the reaction mixture, as a function of the optical density and/or of the change in the optical density and/or of at least one other process parameter.

7. A device for carrying out the method according to claim 1, the device comprising:
    at least one light source, which is positioned and orientated in such a way that the light emitted is configured to enter the reactor along a light path and directly and/or indirectly enter the reaction mixture under the conditions of at least one type of shaking;
    at least one light sensor being positioned and orientated in such a way that it is configured to directly and/or indirectly detect light transmitted entirely through the reactor and/or the reaction mixture and scattered from the reaction mixture in the light path, wherein the at least one light sensor is positioned and orientated in such a way that the detected light has periodic changes due to shaking in at least one of the properties thereof, such as in the intensity thereof, and
    at least one processor and/or the device is operated in combination with at least one processor, at least one processor being used for at least one of the following purposes: recording the measurement values, storing the measurement values, processing the measurement values, representing the measurement values and/or processing results.

8. The device according to claim 7, characterized in that the at least one light source and/or at least one light sensor are combined with
    at least one set of optics having a component selected from the group consisting of a lens, an aperture, a prism, a diffraction grating, an optical gap, a polarizer, an optical filter, and an optical fiber, and/or
    an electronic system for changing the light source intensity or the light sensor sensitivity, and/or
    at least one light sensor, which is positioned and orientated in such a way that it only detects ambient light, but not any light exiting the reactor and/or the reaction mixture.

9. The device according to claim 7, characterized in that the device:
    comprises at least one metering system and/or at least one connection point for at least one metering system for the automated addition of at least one substance to the reaction mixture, and/or
    comprises at least one system and/or at least one connection point for at least one system for temperature-controlling the reactor and/or the reaction mixture, and/or
    communicates with at least one processor via radio and/or wiring, and/or
    draws electrical energy from at least one storage battery and/or another electrical energy source.

10. A system for taking and processing measurements of the optical density and/or the change in the optical density of a reaction mixture in a shaken reactor, characterized in that the system comprises at least one device according to claim 7.

11. The method according to claim 1, characterized in that the at least one light sensor comprises another light sensor, characterized in that the another light sensor detects the scattered light.

12. The method according to claim 1, characterized in that the at least one light sensor comprises a plurality of light sensors forming a light sensor array, the method further characterized in that the step of detecting light scattered from the reaction mixture comprises simultaneously detecting scattered light exiting the reaction mixture at different scattering angles using the light sensor array.

13. A method for determining the optical density and/or the change in the optical density of a reaction mixture in a shaken reactor, comprising the following steps:
providing light from at least one light source that enters the reaction mixture,
detecting light exiting the reaction mixture by at least one light sensor,
shaking the reactor and the reaction mixture during the detection of the light by the at least one light sensor, wherein the light detected by the at least one light sensor is at a frequency such that the shaking frequency is not an integer multiple of the detection frequency,
combining at least two measurement points detected by at least one light sensor in a particular time interval into a series of measurements, and
controlling at least one metering system for adding at least one substance as a function of the optical density and/or of the change in the optical density and/or of at least one other process parameter.

14. The method according to claim 13, characterized in that the detected light is transmitted entirely through the reaction mixture and scattered from the reaction mixture.

15. The method according to claim 13, characterized in that the at least one light sensor comprises a plurality of light sensors forming a light sensor array, the method further characterized in that the step of detecting light comprises simultaneously detecting scattered light exiting the reaction mixture at different scattering angles using the light sensor array.

16. The method according to claim 13, characterized in that
the light is detected by the at least one light sensor at a frequency higher than the shaking frequency, and/or
at least one light path of at least one light source/light sensor pair is orientated non-parallel to a shaking axis and/or shaking plane, and/or
there is no relative movement between the reactor and at least one light sensor.

17. The method according to claim 13, characterized in that, from at least one series of measurements determined in a particular time interval, the optical density and/or the change in the optical density and/or at least one fluid-mechanical parameter and/or at least one fluid-mechanical property of the reaction mixture in the measured time interval is determined by means of at least one suitable mathematical/computing method and/or at least one model function.

18. The method according to claim 13, characterized in that, from at least one series of measurements and/or at least one time series of a parameter of the reaction mixture determined from at least one measurement point and/or at least one series of measurements, at least one further parameter of the reaction mixture is determined by means of at least one suitable mathematical/computing method and/or at least one model function.

19. The method according to claim 13, characterized in that at least one model function is generated afresh and/or modified using at least one suitable mathematical method and/or at least one suitable computing algorithm.

20. The method according to claim 13, further comprising operating at least one further technical system which affects the process, in particular a system for temperature-controlling the reaction mixture, as a function of the optical density and/or of the change in the optical density and/or of at least one other process parameter.

21. A method for determining the optical density and/or the change in the optical density of a reaction mixture in a shaken reactor, comprising the following steps:
providing light from at least one light source that enters the reaction mixture,
simultaneously detecting scattered light exiting the reaction mixture at different scattering angles using a light sensor array comprising a plurality of light sensors,
shaking the reactor and the reaction mixture during the detection of the light by the array, wherein the light detected by the array is at a frequency such that the shaking frequency is not an integer multiple of the detection frequency, and
combining at least two measurement points detected by the array in a particular time interval into a series of measurements.

22. The method according to claim 21, further comprising detecting light transmitted entirely through the reaction mixture that is not scattered and combining at least two additional measurement points detected from the light transmitted entirely through the reaction mixture.

23. The method according to claim 21, characterized in that:
the light is detected at a frequency higher than the shaking frequency, and/or
at least one light path of at least one light source/light sensor pair is orientated non-parallel to a shaking axis and/or shaking plane, and/or
there is no relative movement between the reactor and at least one light sensor.

24. The method according to claim 21, characterized in that, from at least one series of measurements determined in a particular time interval, the optical density and/or the change in the optical density and/or at least one fluid-mechanical parameter and/or at least one fluid-mechanical property of the reaction mixture in the measured time interval is determined by means of at least one suitable mathematical/computing method and/or at least one model function.

25. The method according to claim 21, characterized in that, from at least one series of measurements and/or at least one time series of a parameter of the reaction mixture determined from at least one measurement point and/or at least one series of measurements, at least one further parameter of the reaction mixture is determined by means of at least one suitable mathematical/computing method and/or at least one model function.

26. The method according to claim 25, characterized in that at least one model function is generated afresh and/or modified using at least one suitable mathematical method and/or at least one suitable computing algorithm.

27. The method according to claim 21, further comprising the steps of:

controlling at least one metering system for adding at least one substance as a function of the optical density and/or of the change in the optical density and/or of at least one other process parameter, and/or operating at least one further technical system which affects the process, in particular a system for temperature-controlling the reaction mixture, as a function of the optical density and/or of the change in the optical density and/or of at least one other process parameter.

28. A device for carrying out the method according to claim 13, the device comprising:
    at least one light source, which is positioned and orientated in such a way that the light emitted thereby is configured to enter the reactor and directly and/or indirectly enter the reaction mixture under the conditions of at least one type of shaking,
    at least one light sensor being positioned and orientated in such a way that it is configured to directly and/or indirectly detect light emitted from the reactor and/or the reaction mixture, wherein the at least one light sensor is positioned and orientated in such a way that the light detected thereby and emitted from the reactor and/or the reaction mixture has periodic changes due to shaking in at least one of the properties thereof, optionally in the intensity thereof,
    at least one processor and/or the device is operated in combination with at least one processor, the at least one processor being used for at least one of the following purposes: recording the measurement values, storing the measurement values, processing the measurement values, representing the measurement values and/or processing results; and at least one metering system and/or at least one connection point for at least one metering system for the automated addition of at least one substance to the reaction mixture.

29. The device according to claim 28, characterized in that the at least one light sensor is positioned and orientated in such a way that the at least one light sensor is configured to directly and/or indirectly detect light transmitted through the reaction mixture and scattered from the reaction mixture.

30. The device according to claim 28, characterized in that the at least one light sensor comprises a plurality of light sensors forming a light sensor array configured to simultaneously detect scattered light at various scattering angles from the reactor and/or the reaction mixture, characterized in that the array is positioned and orientated in such a way that the light detected thereby and emitted from the reactor and/or the reaction mixture has periodic changes due to shaking in at least one of the properties thereof, such as in the intensity thereof.

31. The device according to claim 28, characterized in that the at least one light source and/or at least one light sensor are combined with at least one set of optics having a component selected from the group consisting of a lens, an aperture, a prism, a diffraction grating, an optical gap, a polarizer, an optical filter, and an optical fiber, and/or an electronic system for changing the light source intensity or the light sensor sensitivity, and/or at least one light sensor, which is positioned and orientated in such a way that it only detects ambient light, but not any light exiting the reactor and/or the reaction mixture.

32. The device according to claim 28, characterized in that the device:
    comprises at least one system and/or at least one connection point for at least one system for temperature-controlling the reactor and/or the reaction mixture, and/or
    communicates with at least one processor via radio and/or wiring, and/or
    draws electrical energy from at least one storage battery and/or another electrical energy source.

33. A system for taking and processing measurements of the optical density and/or the change in the optical density of a reaction mixture in a shaken reactor, characterized in that the system comprises at least one device according to claim 28.

34. A device for carrying out the method according to claim 21, the device comprising:
    at least one light source, which is positioned and orientated in such a way that the light emitted thereby is configured to enter the reactor and directly and/or indirectly enter the reaction mixture under the conditions of at least one type of shaking,
    a light sensor array comprising a plurality of light sensors configured to simultaneously detect scattered light at various scattering angles from the reactor and/or the reaction mixture, wherein the array is positioned and orientated in such a way that the light detected thereby and emitted from the reactor and/or the reaction mixture has periodic changes due to shaking in at least one of the properties thereof, such as in the intensity thereof, and
    at least one processor and/or the device is operated in combination with at least one processor, the at least one processor being used for at least one of the following purposes: recording the measurement values, storing the measurement values, processing the measurement values, representing the measurement values and/or processing results.

35. The device according to claim 34, further comprising a light sensor positioned and orientated in such a way that it is configured to directly and/or indirectly detect light transmitted entirely through the reactor and/or the reaction mixture that is not scattered.

36. The device according to claim 34, further comprising at least one metering system and/or at least one connection point for at least one metering system for the automated addition of at least one substance to the reaction mixture.

37. The device according to claim 34, characterized in that at least one light source and/or at least one light sensor from the array are combined with at least one set of optics having a component selected from the group consisting of a lens, an aperture, a prism, a diffraction grating, an optical gap, a polarizer, an optical filter, and an optical fiber, and/or an electronic system for changing the light source intensity or the light sensor sensitivity, and/or at least one light sensor, which is positioned and orientated in such a way that it is configured to only detect ambient light, but not any light exiting the reactor and/or the reaction mixture.

38. The device according to claim 34, characterized in that the device:
    comprises at least one system and/or at least one connection point for at least one system for temperature-controlling the reactor and/or the reaction mixture, and/or
    communicates with at least one processor via radio and/or wiring, and/or
    draws electrical energy from at least one storage battery and/or another electrical energy source.

39. A system for taking and processing measurements of the optical density and/or the change in the optical density of a reaction mixture in a shaken reactor, characterized in that the system comprises at least one device according to claim 34.

\* \* \* \* \*